United States Patent [19]
Leopardi et al.

[11] Patent Number: 5,876,923
[45] Date of Patent: Mar. 2, 1999

[54] HERPES SIMPLEX VIRUS ICP4 AS AN INHIBITOR OF APOPTOSIS

[75] Inventors: Rosario Leopardi; Bernard Roizman, both of Chicago, Ill.

[73] Assignee: Arch Development Corporation, Chicago, Ill.

[21] Appl. No.: 690,473

[22] Filed: Jul. 26, 1996

[51] Int. Cl.$^6$ ............................... C12Q 1/70; C12Q 1/68; A01N 63/00; A01N 43/04
[52] U.S. Cl. ............................... 435/5; 435/6; 435/69.2; 424/93.1; 424/93.2; 514/44
[58] Field of Search ........................ 514/44; 424/93.1, 424/93.2; 435/5, 6, 69.2

[56] References Cited

U.S. PATENT DOCUMENTS 5,500,432 3/1996 Nicolaou et al. ..................... 514/281

FOREIGN PATENT DOCUMENTS

WO 95/16779 6/1995 WIPO.

OTHER PUBLICATIONS

International Search Report dated Feb. 3, 1998 (PCT/US97/12904) (ARCD:239P).

Leopardi and Roizman, "Functional interaction and colocalization of the herpes simplex virus 1 major regulatory protein ICP4 with EAP, a nucleolar–ribosomal protein," *Proc. Natl. Acad. Sci. USA*, 93:4572–4576, 1996.

Leopardi and Roizman, "The herpes simplex virus major regulatory protein ICP4 blocks apoptosis induced by the virus or by the hyperthermia," *Proc. Natl. Acad. Sci. USA*, 93:9583–9587, 1996.

Papavassiliou, Wilcox and Silverstein, "The interaction of ICP4 with cell/infected–cell factors and its state of phosphorylation modulate differential recognition of leader sequences in herpes simplex virus DNA," *EMBO Journal*, 10(2):397–406, 1991.

Xia, Knipe and DeLuca, "Role of protein kinase A and the serine–rich region of herpes simplex virus type 1 ICP4 in viral replication," *Journal of Virology*, 70(2):1050–1060, 1996.

Baichwal and Sugden, "Vectors for Gene Transfer Derived from Animal DNA Viruses: Transient and Stable Expression of Transferred Genes,"*In: Gene Transfer*, Kucherlapti (Ed.), New York: Plenum Press, 1986.

Batterson and Roizman, "Characterization of the Herpes Simplex Virion–Associated Factor Responsible for the Induction of α Genes,"*J Virology*, 46(2):371–377, May 1983.

Benevenisty and Reshef, "Direct Introduction of Genes into Rats and Expression of the Genes," *Proc. Natl. Acad. Sci., USA*, 83:9551–9555, Dec. 1986.

Bitter et al., "Expression and Secretion Vectors for Yeast," *Methods in Enzym*, 153:516–444, 1987.

Dubensky et al., "Direct Transfection of Viral and Plasmid DNA into the Liver of Spleen of Mice," *Proc. Natl. Acad. Sci., USA*, 81:7529–7533, Dec. 1984.

Ejercito et al., "Characterization of Herpes Simplex Virus Strains Differing in their Effects on Social Behaviour of Infected Cells," *J Gen Virol*, 2:357–364, 1968.

(List continued on next page.)

*Primary Examiner*—Jeffrey Stucker
*Assistant Examiner*—Hankyel T. Park
*Attorney, Agent, or Firm*—Arnold, White & Durkee

[57] ABSTRACT

The ICP4 protein of herpes simplex virus plays an important role in the transactivation of viral genes. The present invention discloses that ICP4 also has the ability to inhibit apoptosis. This function appears to reside in functional domain distinct from the transactivating function, as indicated by studies using temperature sensitive mutants of ICP4 that transactivating function at elevated temperatures. Also disclosed are methods for inhibition of apoptosis using ICP4 or an ICP4 encoding gene, such as an α4 gene, methods of inhibiting ICP4's apoptosis-inhibiting function, and methods for the production of recombinant proteins and treatment of HSV infections.

8 Claims, 13 Drawing Sheets

OTHER PUBLICATIONS

Faber and Wilcox, "Asociation of the Herpes Simplex Virus Regulatory Protein ICP4 with Specific Nucletide Sequences in DNA," *Nucleic Acids Research*, 14:6067–6083, Nov. 1986.

Fechheimer et al., Transfection of Mammalian Cells with Plasmid DNA by Scrape Loading and Sonication Loading, *Proc. Natl. Acad. Sci., USA*, 84:8463–8467, Dec. 1987.

Ferkol et al., "Regulation of the Phosphoenolpyruvate Carboxykinase/Human Factor IX Gene Introduced Into the Livers of Adult Ratsz by Receptor–Mediated Gene Transfer," *FASEB Journal*, 7:1081–1091, Aug. 1993.

Fetrow and Bryant, "New Programs for Protein Tertiary Structure," *Bio/Technology*, 11:479–484, Apr. 1993.

Fraley et al., "Entrapment of a Bacterial Plasmid in Phospholipid Vesicles: Potential for Gene Transfer," *Proc. Natl. Acad. Sci., USA*, 76(7):3348–3352, 1979.

Ghosh and Bachhawat, "Targeting of Liposomes to Hepatocytes," *In: Liver Diseases Targeted Diagnosis and Therapy Using Specific Receptors and Ligands*, Wu and Wu (Eds.), New York: Marcel Dekker, Inc., 1991.

Glorioso et al., "Development and Application of Herpes Simplex Virus Vectors for Human Gene Therapy," *Annu Rev Mircobiol*, 49:675–710, 1995.

Gopal, "Gene Transfer Method for Transient GeneExpression, Stable Transformation, and Cotransformation of Suspension Cell Cultures," *Molecular and Cellular Biology*, 5(5):1188–1190, May 1985.

Gorczyca et al., "Detection of DNA Strand Breaks in Individual Apoptotic Cells by the in Situ Terminal Deoxynucleotodyl Transferase and Nick Translation Assays," *Cancer Research*, 53:1945–1951, Apr. 1993.

Brutlag et al., "Improved Sensitivity of Biological Sequence Database Searches," *Cabios*, 6(3):237–245, 1990.

Campbell et al., "Identification of Herpes Simplex Virus DNA Sequences which Encode a Trans–acting Polypeptide Responsible for Stimulation of Immediate Early Transcription," *J Mol Biol*, 180:1–19, 1984.

Chen and Okayama, "High–Efficiency Transformation of Mammalian Cells by Plasmid DNA," *Molecular and Cellular Biology*, 7(8):2745–2752, Aug. 1987.

Chou and Fasman, "Conformational Parameters for Amino Acids in Helical, β–Sheet, and Random Coil Regions Calculated from Proteins," *Biochem*, 13(2):211–222, 1974.

Chou and Fasman, "Empirical Predictions of Protein Conformation," *Ann Rev Biochem*, 47:251–276, 1978.

Chou and Fasman, "Prediction of β–Turns," *Biophys J*, 26:367–383, Jun. 1979.

Chou and Fasman, "Prediction of Protein Conformation," *Biochem*, 13(2):222–245, 1974.

Chou and Fasman, "Prediction of the Secondary Structure of Proteins from their Amino Acid Sequence," *In: Advances in Enzymology*, Meister (Ed..), New York: John Wiley & Sons, vol. 47:45–148, 1978.

Chou and Roizman, "The $\gamma_1 34.5$ Gene of Herpes Simplex Virus 1 Precludes Neuroblastoma Cells from Triggering Total Shutoff of Protein Synthesis Characteristic of Programmed Cell Death in Neuronal Cells," *Proc. Natl. Acad. Sci., USA*, 89:3277–3270, Apr. 1992.

Conley et al., "Molecular Genetics of Herpes Simplex Virus," *J Virol*, 37(1):191–206, Jan. 1981.

DeLuca et al., "Isolation and Characterization of Deletion Mutants of Herpes Simplex Virus Type 1 in the Gene Encoding Immediate–Early Regulatory Protein ICP4," *J Virology*, 56(2):558–570, Nov. 1985.

Dixon and Schaffer, "Fine–Structure Mapping and Functional Analysis of Temperature–Sensitive Mutants in the Gene Encoding the Herpes Simplex Virus Type 1 Immediate Early Protein VP175," *J Virology*, 36(1):189–203, Oct. 1980.

Graham and Van Der Eb, "A New Technique for the Assay of Infectivity of Human Adenovirus 5 DNA," *Virology*, 52:456–467, 1973.

Harland and Weintraub, "Translation of mRNA Injected into Xenopus Oocytes is Specifically Inhibited by Antisense RNA," *J Cell Biol*, 101:1094–1099, Sep. 1985.

Henderson et al., "Epstein–Barr Virus–Coded BHRF1 Protein, A Viral Homologue of Bcl–2, Protects Human B Cells from Programmed Cell Death," *Proc. Natl. Acad. Sci., USA*, 90:8479–8483, Sep. 1993.

Herz and Roizman, "The α Promoter Regulator–Ovalbumin Chimeric Gene Resident in Human Cells is Regulated Like the Authentic α 4 Gene After Infection with Herpes Simplex Virus 1 Mutants in α 4 Gene," *Cell*, 33:145–151, May 1983.

Holland et al., "Viral DNA synthesis is Required for the Efficient Expression of Specific Herpes Simplex Virus Type 1 mRNA Species," *Virology*, 101:10–24, 1980.

Honess and Roizman, "Proteins Specified by Herpes Simplex Virus XIII. Glycosylation of Viral Polypeptides," *J Virol*, 16(5):1308–1326, Nov. 1975.

Honess and Roizman, "Regulation of Herpesvirus Macromolecular Synthesis I. Cascade Regulation of the Synthesis of Three Groups of Viral Proteins," *J Virol*, 14(1):8–19, Jul. 1974.

Jameson and Wolf, "The Antigenic Index: A Novel Algorithm for Predicting Antigenic Determinants," *Cabios*, 4(1):181–186, 1988.

Johnson and Kahn, "Peptide Turn Mimetics," *In: Biotechnology and Pharmacy*, New York: Chapman and Hall, Chapter 14:366–378, 1993.

Kaneda et al., "Increased Expression of DNA Conintroduced with Nuclear Protein in Adult Rat Liver," *Science*, 243:375–378, Jan. 1989.

Kato et al., "Expressio of Hepatitis B Virus Surface Antigen in Adult Rat Liver," *J Biol Chem*, 266(6):3361–3364, Feb. 1991.

Klein et al., "High–Velocity Microprojectiles for Delivering Nucleic Acids into Living Cells," *Nature*, 327:70–73, May 1987.

Kristie and Roizman, "α4, The Major Regulatory Protein of Herpes Simplex Virus Type 1, is Stably and Specifically Associated with Promoter–Regulatory Domains of α Genes and of Selected Other Viral Genes," *Proc. Natl. Acad. Sci., USA*, 83:3218–3222, May 1986.

Kristie and Roizman, "DNA–Binding site of Major Regulatory Protein α4 Specifically Associated with Promoter–Regulatory Domains of α Genes of Herpes Simplex Virus Type 1," *Proc. Natl. Acad. Sci., USA*, 83:4700–4704, Jul. 1986.

Kuddus et al., "Relationship Between TATA–Binding Protein and Herpes Simplex Virus Type 1 ICP4 DNA–Binding Sites in Complex formation and Repression of Transcription," *J Virol*, 69(9):5568–5575, Sep. 1995.

Kyte and Doolittle, "A Simple Method for Displaying the Hydropathic Character of a Protein," *J Mol Biol*, 157:105–132, 1982.

Leopardi et al., "Repression of the Herpes Simplex Virus 1 α4 Gene by Its Gene Product (ICP4) Within the Context of the Viral Genome is Conditioned by the Distance and Steroaxial Alignment og the ICP4 DNA Binding Site Relative to the TATA Box," *J Virol*, 69(5):3042–3048, May 1995.

McCarthy et al., "Regulatiom of Apoptosis in Transgenic Mice by Simian Virus 40 T Antigen–Mediated Inactivation of p53," *Proc Natl. Acad Sci, USA*, 91:3979–3983, Apr. 1994.

Michael and Roizman, "Binding of the Herpes Simplex Virus Major Regulatory Protein to Viral DNA," *Proc Natl Acad Sci, USA*, 86:9808–9812, Dec. 1989.

Michael and Roizman, "Repression of the Herpes simplex Virus 1 α4 Gene By Its Gene Product Occurs within the Context of the Viral Genome and is Associated with all Three Identified Cognate Sites," *Proc. Natl. Acad. Sci, USA*, 90:2286–2290, Mar. 1993.

Michael et al., The DNA–Binding Properties of the Major Regulatory Protein α4 of Herpes Simplex Viruses *Science*, 239:1531–1534, Mar. 1988.

Mizrahi, "Production of Human Interferons—An Overview," *Process Biochemistry*, 9–12, Aug. 1983.

Muller, "Binding of the Herpes Simplex virus Immediate–Early Gene Product ICP4 to Its Own Transcription Start Site," *J Virol*, 61(3):858–865, Mar. 1987.

Ridgway, "Mammalian Expression Vectors," *In: Vectors, A Survey of Molecular Cloning Vectors and Their Uses*, Rodriquez and Denhardt (Eds.), Boston: Butterworths, Chapter 24:467–492, 1988.

Rippe et al., "DNA–Mediated Gene Transfer into Adult Rat Hepatocytes in Primary Culture," *Mol Cell Biol*, 10(2):689–695, Feb. 1990.

Roizman and Sears, "Herpes Simplex Viruses and Their Replication," *Fields Virol*, Fields et al. (Eds.), Philadellphia: Lippincott–Raven Publishers, Chapter 72, Third Edition, 2231–2295, 1996.

Sarre, "The Phosphorylation of Eukaryotic Initiation Factor 2: A Principle of Translational Control in Mammalian Cells," *BioSystems*, 22:311–325, 1989.

Shen and Shenk, "Viruses and Apoptosis," *Current Opinion in Genetics and Dev*, 5:105–111, 1995.

Shepart and DeLuca, "A Second–Site Revertant of a Defectve Herpes Simplex Virus ICP4 Protein with Restored Regulatory Actvities and dImpaired DNA–bindings Properties," *J Virol*, 65(2):787–795, Feb. 1991.

Temin, "Retrovirus Vectors for Gene Transfer: Efficient Integration into and Expression of Exogenous DNA in Vertebrate Cell Genomes," *In Gene Transfer*, Kucherlapati (Ed.), New York: Plenum Press, Chapter 6:149–187, 1986.

Tur–Kaspa et al., "Use Electroporation to Introduce Biologically Active Foreign Genes into Primary Rat Hepatocytes," 6(2):716–718, Feb. 1986.

Wagner et al., "Antisense Gene Inhibition by Oligonucleotides Containing C–5 Propyne Pyrimidines," *Science*, 260:1510–1513, Jun. 1993.

Weinberger et al., "Identification of Human Glucocorticoid Receptor Complementary DNA Clones by Epitope Selection," *Science*, 228:740–742, May 1985.

White, "Death–Defying Acts: A Meeting Review on Apoptosis," *Genes & Dev*, 7:2277–2284, 1993.

Wolf et al., "An Integrated Family of amino Acid Sequence Analysis Programs," *CABIOS*, 4(1):187–191, 1988.

Nicolas and Rubenstein, "Retroviral Vectors," *In: Vectors, A Survey of Molecular Cloning Vectors and Their Uses*, Rodriguez and Denhardt (Eds.), Boston: Butterworths, Chapter 25:493–513, 1988.

Nicolau and Sene, "Liposome–Mediated DNA Transfer in Eukaryotic Cells, Dependence of the Transfer Efficiency Upon the Type of Liposomes Used and the Host Cell Cycle Stage," *Biochimica et Biophysica Acta*, 721:185–190, 1982.

Nicolau et al., "Liposomes as Carriers for in Vivo Gene Transfer and Expression," *Methods in Enzymology*, 149:157–176, 1987.

Pan and Griep, "Altered Cell Cycle Regulation in the Lens of HPV–16 E6 or #7 Transgenic Mice: Implications for Tumor Suppressor Gene Function in Development," *Genes & Dev*, 1285–1299, 1994.

Perales et al., "Gene Transfer In Vivo: Sustained Expression and Regulation of Genes Introduced into the Liver by Receptor–Targeted Uptake," *Proc. Natl. Acad. Sci., USA* 91:4086–4090, Apr. 1994.

Phillips et al., "Experience in the Cultivation ofMammalian Cells on the 8000 1 Scale," *In: Large–Scale Mammalian Cell Culture*, Feder and Tolbert (Eds.), New York: Academic Press, 87–95, 1985.

Post et al., "Regulation of α Genes of Herpes Simplex Virus: Expression of Chimeric Genes Produced by Fusion of Thymidine Kinase with α Gene Promoters," *Cell*, 24:555–565, May 1981.

Potter et al., "Enhancer–Dependent Expression of Human κ Immunoglobulin Genes Introduced into Mouse pre–B Lymphocytes by Electroporation," *Proc. Natl. Acad. Sci., USA*, 81:7161–7165, Nov. 1984.

Rao, "The Adenovirus E1A Proteins Induce Apoptosis, Which is Inhibited by the E1B 19–kDa and Bcl–2 Proteins," *Proc. Natl. Acad. Sci., USA*, 89:7742–7746, Aug. 1992.

Ray et al., "Viral Inhibition of Inflammation: Cowpox Virus Encodes an Inhibitor of the Interleukin–1β Converting Enzyme," *Cell*, 69:597–604, May 1992.

Wong, et al., Appearance of β–lactamase Activity in Animal Cell upon Liposome–Mediated Gene Transfer: *Gene*, 10(1980) 87–94.

Wu and Wu, "Evidence for Targeted Gene Delivery to Hep G2 Hepatoma Cells in Vitro," *Biochemistry*, 27:887–892, 1988.

Wu and Wu, "Liver–directed gene Delivery", *Advanced Drug delivery Reviews*, 12(1993) 159–167.

Wu and Wu, "Receptor–Mediated in Vitro Gene Transformation by a Soluble DNA Carrier System," *J Biol Chem*, 262(10):4429–4432, Apr. 1987.

Wyllie et al., "Cell Death: The Significance of Apoptosis," *Int'l Rev Cytology*, 68:251–307, 1980.

Yang et al., "In Vivo and In Vitro Gene Transfer to Mammalian Somatic Cells by Particle Bombardment," *Proc. Natl. Acad. Sci., USA*, 87:9568–9572, Dec. 1990.

Zelenin et al., "High–Velocity Mechanical DNA Transfer of the Chloramphenicolacetyl Transferase Gene into Rodent Liver, Kidney and Mammary Gland Cells in Organ Explants and in Vivo," *FEBS*, 280(1):94–96, Mar. 1991.

Zhu et al., "Human Cytomegalovirus IE1 and IE2 Proteins Block Apoptosis," *J Virol*, 69(12):7960–7970, Dec. 1995.

Leopardi R. et al. Repression of the Herpes simplex virus 1 alpha 4 gene by its gene product (ICP4) within context of the viral genome is conditioned by the distance and stereoaxial alignment of the ICP4 DNA binding site relative to the TATA box, J. Virol, May 1995.

Chou J. et al, The gamma 1 34.5 gene of herpes simplex virus 1 precludes neuroblastoma cells from triggering total shutoff of protein synthesis characteristic of programed cell death in neuronal cells, Proc. Nat'l Acad. Sci. 89:3266–3270, Apr. 1992.

Shen Y. et al. Viruses and apoptosis, Curr. Opin. in Genet. and Dev. 5:105–111, 1995.

```
  1  GCTGCTCCTCCTTCCGCGGCCCCTGGGACTATATGAGCCCGAGGACGCCCGATCGTC     60
     CACACGGAGGCGGCTGCCGACACGGATCCAGACCCGACGCGGGACGCCAGAGACAGA

61  CCGTCAGACGCTCGCCGCGGGACGCGCCGGGAGCGCCGATACGGGAGAAGCGCGGAGGGGATCG    120

121  GCCGTCCCTGTCCTTTTCCCACCCAAGCATCGACCGGTCCGGCTAGTTCCGCGTCGAC    180

181  GGCGGGGGTCGTCGGGGTCCGTGGGTCTCGCCCCCCCCATCGAGAGTCCGTAGGTG    240

241  ACCTACCGTGCTACGTCCGCGTCGCAGCCGTATCCCGGAGGATCGCCCGCATCGGCG    300

301  ATGGGCGTCGGAGAACAAGCAGCCGCCCCGGCTCCCCGGGCCCCACCGACGGGCCGCCC    360

361  MetAlaSerGluAsnLysGlnArgProGlySerProGlyLysArgGlyAlaLeuGlyTyrTrpGlyAlaGluThrGluGlu    420
     ACCCCGAGCCCCAGACCGGCGACGAGCGGGGCCCTCGGGTGGGCGCGGAGAGCGGAGGAG

421  ThrProSerProAspArgAspGluArgGlyArgGlyAlaLeuGlyTyrTrpGlyAlaLeuThrGluGlu    480
     GGCGGGGACGACGCCCGACCACCCCGACCACCCCACCCCGACCTGACGACGCCCGGCGG

481  GlyGlyGlyAspAspProAspHisAspProAspHisProHisAspProHisAspLeuAspAspAlaArgArg    540
```

```
      GACGGGAGGGCCCCGCGGCGGGCACCGAGCGCCGGGAGGACGCCCGGGGACGCCGTCTCG
541 ---------+---------+---------+---------+---------+---------+600
      AspGlyArgAlaProAlaAlaGlyThrAspAlaGlyGluAspAlaGlyAspAlaValSer

CCGCGACAGCTGGCTCTGCTGCCTCCATGGTAGAGGAGGCCGTCCGGACGATCCCGACG
601 ---------+---------+---------+---------+---------+---------+660
      ProArgGlnLeuAlaLeuLeuAlaSerMetValGluGluAlaValArgThrIleProThr

CCCGACCCCGCGCCTGCCGCCCCCGGACCCCGCCTTTGAGCCGACGACGATGACGGG
661 ---------+---------+---------+---------+---------+---------+720
      ProAspProAlaAlaSerProProArgThrProAlaPheArgAlaAspAspAspAspGly

GACGAGTACGACGAGCCAGCCGGGCGTATCCGGACCCCACGGACCGCCTGTCGCCGCCCG
721 ---------+---------+---------+---------+---------+---------+780
      AspGluTyrAspAspAlaAlaAspAlaAlaGlyAspArgAlaProAlaArgGlyArgGlu

CGGGAGGCCCCGGTACGCGGGAGACGTCGTCACGGCCGGTGGGCCATGGGGTCATCGACC
781 ---------+---------+---------+---------+---------+---------+840
      ArgGluAlaProLeuArgGlyArgArgHisGlyArgAlaTyrProAspProThrAspArgProProThrAspArgLeuSerProArgPro

CCGGCCCAGCCGCGGGAGCCGGAGACGTCGTCACGGCCGGTGGGCCATGGGGTCATCGACC
841 ---------+---------+---------+---------+---------+---------+900
      ProAlaGlnProProArgArgArgArgHisGlyArgTrpArgProSerAlaSerSerThr

TCGTCGGACTCCGGGTCCTCCGTCCTCGTCCGCATCCTCTTCGTCCTCGTCGTCCGAC
901 ---------+---------+---------+---------+---------+---------+960
      SerSerAspSerGlySerSerSerSerAlaSerSerSerSerSerAsp
```

FIG. 2C

```
     GAGGACGAGGAGGACGGCAACGACGCGGCCGACCACGCGGAGGCGGCGGGCCGTC
961  ---------+---------+---------+---------+---------+---------+1020
     GluAspGluAspAspGlyAsnAspAlaAlaAspHisAlaArgGluAlaAlaArgAlaVal

GGGCGGGGTCCGTCGAGCGCCGGCGGCCAGCGCGGACGCCGCTCCGCCCCGGG
1021 ---------+---------+---------+---------+---------+---------+1080
     GlyArgGlyProSerSerAlaAlaProAlaAlaProGlyArgThrProProProGly

CCACCCCCCCTCTCCGAGGCCGCGCCCAAGCCCCGGGCGGCGGAGGACCCCGCGGCC
1081 ---------+---------+---------+---------+---------+---------+1140
     ProProLeuSerGluAlaAlaProLysProArgAlaAlaAlaArgThrProAlaAla

TCCGCGGGCCGCATCGAGCGCCGGCGCGCGGGTGGCCGGCCGACGCCACG
1141 ---------+---------+---------+---------+---------+---------+1200
     SerAlaGlyArgIleGluArgArgArgAlaArgAlaValAlaAlaGlyArgAspAlaThr

GGCCGGCTTCACGGCCGGGCAGCCCCGGGGTCGAGCTGGACGCCGACCTCCGGC
1201 ---------+---------+---------+---------+---------+---------+1260
     GlyArgPheThrAlaGlyGlnProArgArgValGluLeuAspAlaAspAlaThrSerGly

GCCTTCTACGCGCTATCGCGACGGGTACGTCAGCGGGGAGCCGTGGCCCGGCGCCGGG
1261 ---------+---------+---------+---------+---------+---------+1320
     AlaPheTyrAlaArgTyrArgAspGlyTyrValSerGlyGluProTrpProGlyAlaGly
```

FIG. 2D

```
      CCCCCGCCCCCGGGGGGGGTGCTGTACGGGCGGCCTGGGGACAGCCGCCCGGGCCTCTGG
1321  ------+---------+---------+---------+---------+---------+  +1380
      ProProProGlyArgValLeuTyrGlyLeuGlyAspSerArgProGlyLeuTrp

GGGGCGCCCGAGGGGGAGGAGGCGGACGCCGGTTCGAGGCCTCGGGCGCCCGGCGGCC
1381  ------+---------+---------+---------+---------+---------+  +1440
      GlyAlaProGluAlaGluAlaArgArgPheGluAlaSerGlyAlaProAlaAla

GTGTGGGCGCCCGAGCTGGGCGACGCCGGCAGCAGTACGCCCTGATCACGGGCTGCTG
1441  ------+---------+---------+---------+---------+---------+  +1500
      ValTrpAlaProGluLeuGlyAspAlaAlaAlaGlnTyrAlaLeuIleThrArgLeuLeu

TACACCCCGGACGCGGGAGGCCATGGGGTGGCTCCAGAACCCGCGTGGTCCCCGGGAC
1501  ------+---------+---------+---------+---------+---------+  +1560
      TyrThrProAspAlaGluAlaMetGlyTrpLeuGlnAsnProArgValValProGlyAsp

GTGGCGCTGGACCAGGCCTGCTTCCGGATCTCCGGGCGCGGCAACAGCAGCTCCTTC
1561  ------+---------+---------+---------+---------+---------+  +1620
      ValAlaLeuAspGlnAlaCysPheArgIleSerGlyAlaAlaArgAsnSerSerPhe

ATCACCGGACGCAGCGTGGCCGCGGCCGTGCCCCACCTGGGCTACGCCATGGCGGCCGC
1621  ------+---------+---------+---------+---------+---------+  +1680
      IleThrGlySerValAlaArgAlaValProHisLeuGlyTyrAlaMetAlaAlaGlyArg
```

FIG. 2E

```
      TTCGGCTGGGGCCTGGGCGCACGCGGGGCCCGCGCCGTGGCCATGAGCCGCCGATACGACCGC
1681- - - - -+- - - - - - - - -+- - - - - - - - -+- - - - - - - - -+- - - - - - - - -+- - - - - - - - -+- - - - - - - - - +1740
      PheGlyTrpGlyLeuAlaHisAlaAlaAlaAlaValAlaAlaMetSerArgArgTyrAspArg

GCGCAGAAGGGCTTCCTGCTGACCAGCCTGCGCCGGCCTACGCGCCCCTGTTGGCGCGC
1741- - - - -+- - - - - - - - -+- - - - - - - - -+- - - - - - - - -+- - - - - - - - -+- - - - - - - - -+- - - - - - - - - +1800
      AlaGlnLysGlyPheLeuLeuThrSerLeuArgArgAlaTyrAlaProLeuLeuAlaArg

GAGAACGCGGCTGACGGGGCCGGCGGGAGCCCCGGCGCCGGCGCAGATGACGAGGGG
1801- - - - -+- - - - - - - - -+- - - - - - - - -+- - - - - - - - -+- - - - - - - - -+- - - - - - - - -+- - - - - - - - - +1860
      GluAsnAlaAlaLeuThrGlyAlaAlaGlySerProGlyAlaGlyAlaAspAspGluGly

GTCGCCGCCGTCGCCGCCGCCGCCGCCGCACCGGGCCGGCGGTGCCCGGGTACGGCGCC
1861- - - - -+- - - - - - - - -+- - - - - - - - -+- - - - - - - - -+- - - - - - - - -+- - - - - - - - -+- - - - - - - - - +1920
      ValAlaAlaValAlaAlaAlaAlaAlaAlaProGlyGluArgAlaValProAlaGlyTyrGlyAla

GCGGGGATCCTCGCCGCCCCTGGGGCGGCTGTCCGCCGCCCGCCTTCCCCGCGGGGGC
1921- - - - -+- - - - - - - - -+- - - - - - - - -+- - - - - - - - -+- - - - - - - - -+- - - - - - - - -+- - - - - - - - - +1980
      AlaGlyIleLeuAlaAlaLeuGlyArgLeuSerAlaAlaProAlaSerProAlaGlyGly

GACGACCCCGACGCCCCGCCCACGCCGACGCCGACGACGACGCCGGGCGCCGGCCCAG
1981- - - - -+- - - - - - - - -+- - - - - - - - -+- - - - - - - - -+- - - - - - - - -+- - - - - - - - -+- - - - - - - - - +2040
      AspAspProAspAlaAlaArgHisAlaAspAlaAspAspAlaGlyArgArgAlaGln
```

```
2041 GCCGGCCGCGTGGCCGTCGAGTGCCTGGCCGCCTGCCGCGGGATCCTGGAGGGCTGGCC +2100
     AlaGlyArgValAlaValGluCysLeuAlaAlaCysArgGlyIleLeuGluAlaLeuAla

2101 GAGGGCTTCGACGGCGACCTGGCGGCCGTCCCGGGGCTGGCCGGGGCCCGGCCGCCAGC +2160
     GluGlyPheAspGlyAspLeuAlaAlaValProGlyLeuAlaGlyAlaArgProAlaSer

2161 CCCCCGGCCCGGAGGGACCCGGCCCCGCTTCCCCGCCCTGGCCCCGCACGCCGACGCG +2220
     ProProArgProGluGlyProAlaGlyProAlaSerProProHisAlaAspAla

2221 CCCCGCCTGCGCGTGGCCTGCGCGAGCTGCGGTTCGTGCGGACGCGCTGGTGCTCATG +2280
     ProArgLeuArgAlaTrpLeuArgGluLeuArgPheValArgAspAlaLeuValLeuMet

2281 CGCCTGCGCGGGGACCTGCGCGTGGCCGGCGTGGCCGAGGCCCGCCGTGGCCGCCGTGCGC +2340
     ArgLeuArgGlyAspLeuArgValAlaGlySerGluAlaAlaValAlaAlaValArg

2341 GCCGTGAGCCTGGTCGCCGGCTACGCCCTGGGCCCCGGGGACCCGCGCCTGCCG +2400
     AlaValSerLeuValAlaGlyAlaLeuGlyProArgAspProArgLeuPro
```

```
     AGCTCCGGGGCCGCGGCCGCGGGGACCTGCTGTTTGACAACCAGAGCCTGGCGCCCCTG
2401 ------+---------+---------+---------+---------+---------+ +2460
      SerSerAlaAlaAlaAlaAlaAspLeuLeuPheAspAsnGlnSerLeuArgProLeu

CTGGGGGCGGCGGCCAGGCACCGGACGCGCCGGACGCGCTGGGCCGCGCCGCGCCTCC
2461 ------+---------+---------+---------+---------+---------+ +2520

GCCGCGCCGCGGGAGGGGCGCAAGGCAAGAGTCCCGGCCCCGGCCCGGCCCGGAGGC
2521 ------+---------+---------+---------+---------+---------+ +2580
      AlaAlaProArgGluGlyArgLysArgLysSerProGlyProAlaArgProProGlyGly

GGCGGCCCGGACCCCGAAGACGAAGAAGAGCGGCGGGACGCCCCCGGCTCGGACGCC
2581 ------+---------+---------+---------+---------+---------+ +2640
      GlyGlyProArgProProLysThrLysLysSerGlyAlaAspAlaProGlySerAspAla

CGCGCCCCCCTCCCCGGCCCGCTCCCCGCCCCCAGCCCCGGGGCCCGAGCCCGCCCC
2641 ------+---------+---------+---------+---------+---------+ +2700
      ArgAlaProLeuProAlaProProSerThrProProGlyProGluProAlaPro

GCCCAGCCCGCGGCCCGCGGCCGCGGGGCCGCGCAGGCCCGCGCCCCGTGGCCGTG
2701 ------+---------+---------+---------+---------+---------+ +2760
      AlaGlnProAlaAlaProArgAlaAlaAlaAlaGlnAlaArgProArgProValAlaVal
```

```
         TCGGCCGGCCGCCGAGGGCCCCGACCCCCTGGGCGGACTGGCGGGGGACAGCCCCCGGGG
2761    ---------+---------+---------+---------+---------+---------+  +2820
         SerArgProAlaGluGlyProAspProLeuGlyGlyTrpArgArgGlnProProGly

CCCAGCCACACGGGGCCGCCCGGCGGGCCGCCCGCGCCCTGGAGGCCTACTGCTCCCGCGCC
2821    ---------+---------+---------+---------+---------+---------+  +2880
         ProSerHisThrAlaAlaProAlaAlaAlaAlaLeuGluAlaAlaTyrCysSerProArgAla

GTGGCCGAGCTCACGGACCACCCGCTGTTCCCCGTCCCCTGGCGACCGGCCCTCATGTTT
2881    ---------+---------+---------+---------+---------+---------+  +2940
         ValAlaGluLeuThrAspHisProLeuPheProValProTrpArgProAlaLeuMetPhe

GACCCGCGGGCCCCTGGCCCTCGATCGCCGCCGGGTGCGCCGCCCCCCGCCGCCCAG
2941    ---------+---------+---------+---------+---------+---------+  +3000
         AspProArgAlaLeuAlaSerIleAlaAlaArgCysAlaAlaArgCysAlaAlaProAlaAlaGln

GCCGCGGTGCGCGGCGGGGGCGGCGACGAGGAGATAACCCCCACCCCACGGGGCCGCCGGGGGC
3001    ---------+---------+---------+---------+---------+---------+  +3060
         AlaAlaCysGlyGlyGlyGlyAspAspAspAspAsnProHisProHisGlyAlaAlaGlyGly

CGCCTCTTTTGGCCCCCCTGCGCGCCTGGGCCCTGCGACCCGGCCGCATGGCGGCCTGGATGCGC
3061    ---------+---------+---------+---------+---------+---------+  +3120
         ArgLeuPheGlyProLeuArgArgMetAlaAlaTrpMetArg
```

```
      CAGATCCCCGACCCCGAGGACGTGCGCGTGGTGGTGCTGTACTCGCCGCTGCCGGGCGAG
3121 ----+----+----+----+----+----+----+----+----+----+----+----+ +3180
      GlnIleProAspProGluAspValArgValValValLeuTyrSerProLeuProGlyGlu

GACCTGGCCGGCGGGGGCCTCGGGGGGCCGCCCGGAGTGGTCCGCGAGCGGCGGGGGG
3181 ----+----+----+----+----+----+----+----+----+----+----+----+ +3240
      AspLeuAlaGlyGlyGlyAlaSerGlyGlyProProGluTrpSerAlaGluArgGlyGly

CTGTCCTGCCTGCTGGCCCTGGCCAACCGGCTGTGCGGCGGACACGGCCGCCTGG
3241 ----+----+----+----+----+----+----+----+----+----+----+----+ +3300
      LeuSerCysLeuLeuAlaAlaLeuAlaAsnArgLeuCysGlyProAspThrAlaAlaTrp

GCGGGCAATTGGACCGGCCCCCGACGTGTCGGCGCTGGGCGCTGGGCGCACAGGGCGTGTGCTG
3301 ----+----+----+----+----+----+----+----+----+----+----+----+ +3360
      AlaGlyAsnTrpThrGlyAlaProAspValSerAlaLeuGlyAlaGlnGlyValLeuLeu

CTGTCCAGCGGGGACCTGGCCTTCGCCGGCCGTGGAGTTTCTGGGGCTGCTCGCCAGC
3361 ----+----+----+----+----+----+----+----+----+----+----+----+ +3420
      LeuSerThrArgAspLeuAlaPheAlaGlyAlaValGluPheLeuGlyLeuLeuAlaSer

GCCGGGGACCGGCGGCTCATCGTGGTCAACACCGTGCGCGCCTGCGACTGGCCCGCCGAC
3421 ----+----+----+----+----+----+----+----+----+----+----+----+ +3480
      AlaGlyAspArgArgLeuIleValValAsnThrValArgAlaCysAspTrpProAlaAsp
```

FIG. 2J

```
      GGGCCCGGCGGTGTCGGGGCAGCAGCGCCTACCTGGCGTGCGAGCTGCTGCCCGCGTGCAG
3481 ----------+---------+---------+---------+---------+---------+ +3540
      GlyProAlaValSerArgGlnHisAlaTyrLeuAlaCysGluLeuLeuProAlaValGln

TGCGCCGTGCGCTGGCCGGCGGCGGGGACCTGCGCCGCACGTGCTGGCCTCGGGCCGC
3541 ----------+---------+---------+---------+---------+---------+
 +3600CysAlaValArgTrpProAlaAlaArgAspLeuArgArgThrValLeuAlaSerGlyArg

GTGTTCGGACCCGGGGGTCTTCGCGGCGTGGAGGCCGCGCACGCGCCTGTACCCCGAC
3601 ----------+---------+---------+---------+---------+---------+ +3660
      ValPheGlyProGlyValPheAlaArgValGluAlaAlaHisAlaArgLeuTyrProAsp

GCGCCGCCGCTGCGCCTGTGCCGGGGCGGCAACGTGGCGTACCGGTGCCACGCGCTTC
3661 ----------+---------+---------+---------+---------+---------+ +3720
      AlaProProLeuArgLeuCysArgGlyGlyAsnValArgTyrArgValArgThrArgPhe

GGCCCGGACACGCCGGTGCCCATGTCCCCGCGGAGTACCGCGGGCCGTGCTGCCGGCG
3721 ----------+---------+---------+---------+---------+---------+ +3780
      GlyProAspThrProValProMetSerProArgGluTyrArgArgAlaValLeuProAla

CTGGACGGCCGGGCGGCGGCGAGCGGCCTCGGGGACCACCGACGCCATGGCGCCCGGGGCGGCCGGAC
3781 ----------+---------+---------+---------+---------+---------+ +3840
      LeuAspGlyArgAlaAlaAlaSerGlyThrThrAspAlaMetAlaProGlyAlaProAsp
```

FIG. 2K

```
     TTCTGCGAGGAGGAGGCCCACTCGCCACGCCGCCTGCCGCGCTGGGCCTGGGCCGGCCG
3841 ---------+---------+---------+---------+---------+---------+ +3900
      PheCysGluGluAlaHisSerHisAlaAlaCysAlaArgTrpGlyLeuGlyAlaPro

CTGCGGCCCGTGTACGTGGGCGCTGGGCGGCGGAGGGTGCGCGCCGGCCCGGCCCGGTGG
3901 ---------+---------+---------+---------+---------+---------+ +3960
      LeuArgProValTyrValAlaLeuGlyArgGluAlaValArgAlaGlyProAlaArgTrp

CGCGGGGCCGCGGAGGGACTTTTGCGCCCCGCCCTGCTGGAGCCCGACGACGAGGACGCCCCC
3961 ---------+---------+---------+---------+---------+---------+ +4020
      ArgGlyProArgArgAspPheCysAlaArgAlaLeuLeuGluProAspAspAspAlaPro

CCGCTGGTGCTGCGCGGGGACGACGGGCCCCTGCCGCGCCCTGCCGGCGCCGCCCGGG
4021 ---------+---------+---------+---------+---------+---------+ +4080
      ProLeuValLeuArgGlyAspAspGlyProAlaLeuProProAlaProProGly

ATTCGCTGGGCCTCGGCCACGGGCCAGCGGCACCGTGCTGGCGGCGGCGGGGGCCGTG
4081 ---------+---------+---------+---------+---------+---------+ +4140
      IleArgTrpAlaSerAlaThrGlyArgSerGlyTyrValLeuAlaAlaAlaGlyAlaVal
```

```
                GAGGTGCTGGGGGCGGAGGCGGGCTTGGCCACGCCCCCGCGCGGGAAGTTGTGGACTGG
4141------+---------+---------+---------+---------+---------+----+4200
                GluValLeuGlyAlaGluAlaGlyLeuAlaThrProArgArgGluValValAspTrp

GAAGGCGCCTGGGACGAAGACGACGGCGGCGCGTTCGAGGGGACGGGGTGCTGTAA       (SEQ ID NO: 1)
4201------+---------+---------+---------+---------+---------+---- 4257
                GluGlyAlaTrpAspGluAspAspGlyGlyAlaPheGluGlyAspGlyValLeu***      (SEQ ID NO: 2)
```

HERPES SIMPLEX VIRUS ICP4 AS AN INHIBITOR OF APOPTOSIS

The government may own certain rights in this application by virtue of federal funding under grant numbers AI124009 (NIAID) and CA47451 (NCI).

BACKGROUND OF THE INVENTION

I. Field of the Invention

The present invention relates to the fields of molecular and cell biology generally, and more specifically, it addresses mechanisms for growth control in eurkaryotic cells. In particular, there are provided viral genes that inhibit normal cell death and methods for use thereof.

II. Related Art

The control of host cell gene expression, and often the control of genes involved in DNA replication, are integral parts of the life cycle of a virus. However, recent evidence suggests that most eukaryotic cells respond to viral disruption of normal cellular physiology by undergoing programmed cell death (apoptosis) (White, 1993). To counteract this, many viruses have evolved mechanisms to block host cell death (Clem and Miller, 1994; White and Gooding, 1994). In several cases, viral genomes have been found to contain genes whose products interact with proteins that play a central role in regulating cell survival.

Programmed cell death is triggered by several factors and may take various forms. For example, the synthesis of double-stranded RNA activates kinases which phosphorylate the $\alpha$ subunit of eIF-2 and completely turn off protein synthesis (Sarrel, 1989). Ultimately, activation of metabolic pathways causes a pattern of morphological, biochemical, and molecular changes which result in cell death without spillage of cellular constituents which would result in an inflammatory response detrimental to the host (Wyllie, et al.).

Apoptotic cell death is commonly observed during embryogenesis and organ involution and in the natural death of terminally differentiated cells at the end of their life span. Most viruses which induce either the shut-off of protein synthesis or apoptosis also have evolved mechanisms which block host responses and enable them to replicate in their hosts (Shen and Shenk, 1995). Among the best-known examples of viral gene products which block apoptosis are the adenovirus EIB $M_r$19,000 protein (Rao, et al, 1992.), vaccinia CrmA protein (Ray, et al.), simian virus 40 (SV40) T antigen (McCarthy, et al., 1994), human papillomavirus No. 16 (HPV 16) E6 protein (Pan and Griep, 1994), Epstein-Barr virus BHRF1 protein (Henderson, et al., 1993) and human cytomegalovirus IE1 and IE2 gene products (Zhu, et al., 1995). Herpes simplex virus 1 (HSV-1) encodes a protein, $\gamma_1$34.5, which blocks the phosphorylation of eIF-2$\alpha$ (Chou and Roizman, 1992).

The utility of proteins that are capable of inhibiting apoptosis are manifold. First, such proteins, or their corresponding genes, may be used to immortalize cell lines that otherwise would perish during culture. This makes possible not only the study of these cells, but also presents the option of growing these cells in large numbers in order to isolate protein species therefrom. Second, the identification of inhibitors of apoptosis and their function permits the possible intervention, in a clinical setting, when these proteins are interfering with normal programmed cell death, or apoptosis. This may be accomplished by providing an inhibitor or an antisense nucleic acid that interferes with the expression of a protein that interferes with apoptosis. Thus, the identification of novel proteins having these activities and uses provide important new tools for those working in this arena.

SUMMARY OF THE INVENTION

It is, therefore, an object of the present invention to provide methods for the use of infected cell protein number 4, or ICP4, and its cognate gene $\alpha$4, as inhibitors of apoptosis. In addition, it is an object of the present invention to provide methods for the use of agents that inhibit ICP4 and/or $\alpha$4 in order to induce apoptosis in HSV infected cells. It also is an object of the present invention to provide methods for the identification of agents that inhibit the apoptosis-inhibiting function of ICP4.

In satisfying these goals, there is provided a method for blocking apoptosis of a cell comprising the step of providing to the cell an HSV ICP4 polypeptide or an HSV$\alpha$4 gene. The $\alpha$4 gene may be contained in an expression vector and, further, under the control of a promoter active in eukaryotic cells. One such promoter is the a tetracycline controlled promoter. The expression vector further comprises a selectable marker and/or further comprises a gene encoding a second polypeptide under the transcriptional control of a promoter active in eukaryotic cells.

In another embodiment, there is provided a method for inducing apoptosis in a cell infected with HSV comprising the step of administering to said cell an agent that inhibits HSV ICP4 function in said cell. The agent may inhibit transcription or translation of an HSV $\alpha$4 gene or transcript or may bind to an HSV ICP4 polypeptide. The reagent may be an antisense HSV $\alpha$4 construct an antibody that binds immunologically to an HSV ICP4 polypeptide. Particular antisense constructs are oligonucleotides that hybridizes to a 5'-untranslated region for an HSV $\alpha$4 gene or a translational start site for an HSV $\alpha$4 transcript. Particular antibodies are polyclonal sera against ICP4 or a monoclonal antibody against ICP4.

In yet another embodiment, there is provided a method for treating a subject with an HSV infection comprising the step of inhibiting HSV ICP4 function. The inhibition may comprise providing to the subject a first pharmaceutical composition comprising an HSV $\alpha$4 antisense construct or a monoclonal antibody that binds immunologically to an HSV ICP4 polypeptide. The first pharmaceutical composition may be applied topically to HSV infected cells in said patient. The method may further comprise the step of providing to said subject a second pharmaceutical composition comprising a conventional anti-HSV agent, such as acyclovir. Acyclovir is delivered via a route selected from the group consisting of topically, orally and intravenously.

In yet still another embodiment, there is provided a screening method for compounds having inhibitory activity against HSV ICP4 polypeptide-induced inhibition of apoptosis comprising the steps of (a) providing a first cell comprising an HSV $\alpha$4 gene under the control of an HSV immediate early promoter; (b) infecting said first cell with a herpes simplex virus that lacks a functional $\alpha$4 gene; (c) contacting said first cell with a test compound; (d) incubating said first cell under conditions permitting viral replication; and (e) comparing the cell pathology of said first cell following incubation with the cell pathology of a second cell that lacks an HSV $\alpha$4 gene following infection with said herpes simplex virus and the cell pathology of a third cell comprising an HSV $\alpha$4 gene under the control of an HSV immediate early promoter following infection with said herpes simplex virus but in the absence of said test compound. Cell pathology comprises condensation of chromatin, obliteration of nuclear membranes, vacuolization, cytoplasmic blebbing and DNA fragmentation.

The screening method may employ a cell line which contains an integrated copy of a wild-type HSV α4 gene under the control of an α4 promoter and a herpes simplex virus that lacks a functional HSV α4 gene has a deletion in both copies of the virally-encoded α4 genes. For example, the herpes virus may carry a temperature sensitive mutation in both copies of the virally-encoded α4 gene; incubation is at 39.5° C.

Another screening method for compounds having inhibitory activity against HSV ICP4-induced inhibition of apoptosis comprises the steps of (a) providing a first cell comprising an HSV α4 gene under the control of an inducible promoter; (b) inducing transcription from said promoter; (c) contacting said first cell with a test compound; (d) incubating said first cell under conditions expression of an HSV ICP4 polypeptide; and (e) comparing the cell pathology of said first cell following incubation with the cell pathology of a second cell not having an HSV α4 gene following induction and the cell pathology of a third cell comprising an HSV α4 gene under the control of an inducible promoter following induction but in the absence of said test compound.

Yet another screening method for compounds having inhibitory activity against HSV ICP4 polypeptide-induced inhibition of apoptosis comprises the steps of (a) providing a first cell; (b) infecting said first cell with a herpes simplex virus; (c) contacting said first cell with a test compound; (d) incubating said first cell under conditions permitting viral replication; and (e) comparing the cell pathology of said first cell following incubation with the cell pathology of a second cell treated with said test compound alone and the cell pathology of a third cell following infection with said herpes simplex virus but in the absence of said test compound.

In still yet a further embodiment, there is provided a method for expressing a polypeptide in a cell comprising the steps of (a) contacting a cell with a herpes virus vector encoding said polypeptide; (b) contacting said cell with an agent that blocks the transactivating function of ICP4 but does not block the apoptosis inhibiting function of ICP4.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A–L: Nucleotide and amino acid sequence of α4 and ICP4, respectively.

DETAILED DESCRIPTION OF THE INVENTION

I. Herpes Simplex Virus

Figure 1:
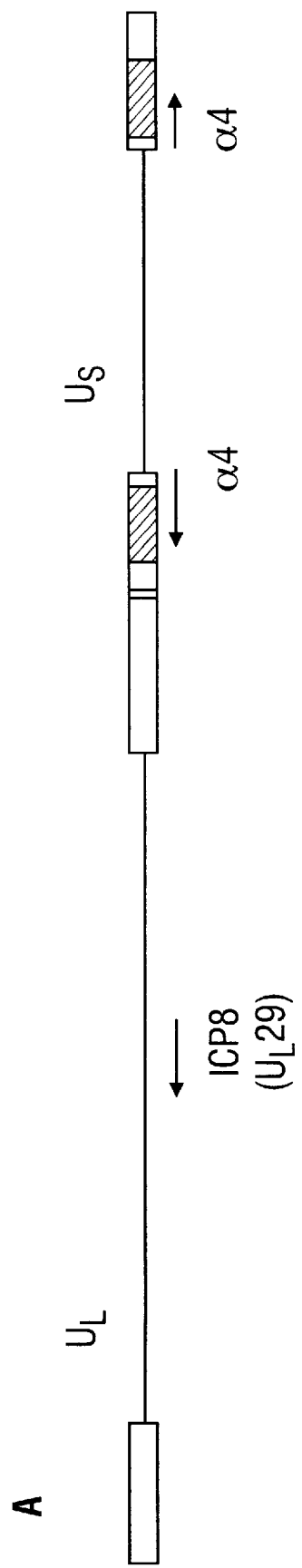
FIG. 1: Diagrammatic representation of the HSV-1 genome showing the location of the α4 and $U_L29$ genes encoding ICP4 and ICP8, respectively. The reiterated sequences (open rectangles) flanking the unique short ($U_S$) and unique long ($U_L$) sequences (thin lines) and the location and direction of genes are as shown. Because the α4 gene maps within inverted repeats flanking the $U_L$, it is present in two copies per genome. The hatched lines within the rectangles indicates the position of the sequences deleted from the d120 mutant (DeLuca, et al., 1985).

Herpes simplex viruses, designated with subtypes 1 and 2, are enveloped viruses that are among the most common infectious agents encountered by humans, infecting millions of human subjects worldwide. These viruses cause a broad spectrum of disease which ranges from relatively insignificant to severe and life-threatening. Clinical outcome of herpes infections is dependent upon early diagnosis and prompt initiation of antiviral therapy. Despite some successful efforts in treating HSV infectious, dermal and epidermal lesion often recur, and HSV infections of neonates and infections of the brain are associated with high morbidity and mortality.

The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transinducing factor (Post et al., 1981; Batterson and Roizman, 1983; Campbell, et al., 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle.

II. The ICP4 Polypeptide

As stated above, the expression of β genes is regulated in a major fashion by ICP4 (DeLuca et al., 1985), and therefore this gene has a distinct effect on viral DNA synthesis. γ genes, a heterogeneous group of genes encoding largely virion structural proteins, require the onset of viral DNA synthesis for optimal expression (Honess and Roizman, 1975; Holland et al., 1980). ICP4 plays a key role in this process—cells infected with viruses carrying temperature sensitive mutations in the α4 gene and maintained at nonpermissive temperatures express largely α proteins (Dixon and Shaffer, 1980). Furthermore, studies involving shift-up of infected cells from permissive to nonpermissive temperatures have confirmed a key role for ICP4 throughout the viral reproductive cycle.

ICP4 acts both as a transactivator and as a repressor (Roizman and Sears, 1995). The response elements for the repressor functions of ICP4 are high affinity binding sites located in the proximity of transcription initiation sites of the genes repressed by the protein (Kristie and Roizman, 1986a, Kristie and Roizman, 1986b, Faber and Wilcox, 1986, Muller, 1987, Michael and Roizman, 1989, Michael and Roizman, 1993). The strength of repression is dependent on both the distance and stereoaxial alignment with the TATA box (Leopardi et al., 1995, Kuddus et al., 1995). Low affinity sites for binding of ICP4 have also been documented, but their function is less well understood (Kristie and Roizman, 1986a, Kristie and Roizman, 1986b, Michael et al., 1988). The response elements thought to act in the transactivation of viral genes by ICP4 are not known, but mutations in ICP4 may affect repression and activation independently of each other (Shepard and DeLuca, 1991).

According to the present invention, a novel functional aspect of ICP4 previously undisclosed is its ability to inhibit apoptosis. Apoptosis, or programmed cell death, is characterized by certain cellular events, including nuclear condensation, DNA fragmentation, cytoplasmic membrane blebbing and, ultimately, irreversible cell death. Apoptosis is an energy-dependent event. For the purposes of this application, apoptosis will be defined as inducing one or more of these events. Thus, the use of the term "ICP4" in this application encompasses polypeptides having the anti-apoptosis function of ICP4. These need not be wild-type ICP4.

This functional attribute is manifested, for example, in ICP4's ability to protect cells from apoptosis triggered by modification of cellular physiology by other viral genes. This observation permits utilization of ICP4 in a number of ways that could not have been predicted from the prior art. For example, according to the present invention, the production of HSV vectors or recombinant proteins from HSV vectors can be enhanced by increasing the apoptosis inhibiting function of ICP4. When cells are infected with HSV, premature cell death can limit the titer of virus produced or the amount of recombinant protein synthesized. Similarly, ICP4 may prolong the life of the cells expressing human or animal genes introduced into cells by viral vectors in order to correct genetic defect. If the cell can be sustained longer, the titer of the virus stocks and the amount of protein should increase.

ICP4 may be obtained according various standard methodologies that are known to those of skill in the art. For example, antibodies specific for ICP4 may be used in immunoaffinity protocols to isolate ICP4 from infected cells, in particular, from infected cell lysates. Antibodies are advantageously bound to supports, such as columns or beads, and the immobilized antibodies can be used to pull the ICP4 target out of the cell lysate.

Alternatively, expression vectors, rather than viral infections, may be used to generate ICP4. A wide variety of expression vectors may be used, including viral vectors. The structure and use of these vectors is discussed further, below. Such vectors may significantly increase the amount of ICP4 protein in the cells, and may permit less selective purification methods such as size fractionation (chromatography, centrifugation), ion exchange or affinity chromatograph, and even gel purification. Alternatively, the expression vector may be provided directly to target cells, again as discussed further, below.

ICP4, according to the present invention, may advantageously be cleaved into fragments for use in further structural or functional analysis, or in the generation of reagents such as ICP4-related polypeptides and ICP4-specific antibodies. This can be accomplished by treating purified or unpurified ICP4 with a peptidase such as endoproteinase glu-C (Boehringer, Indianapolis, Ind.). Treatment with CNBr is another method by which ICP4 fragments may be produced from natural ICP4. Recombinant techniques also can be used to produce specific fragments of ICP4. Because the transactivating and apoptosis-inhibiting functions of ICP4 appear to reside in distinct domains, the ability to make domain-specific reagents now has significance. For example, the ability to provide an apoptosis-inhibiting ICP4 fragment that does not transactivate viral genes may prove to be effective in extending the life of neurons expressing compensatory or therapeutic genes from a viral vector.

It is expected that changes may be made in the sequence of ICP4 while retaining a molecule having the structure and function of the natural ICP4. For example, certain amino acids may be substituted for other amino acids in a protein structure without appreciable loss of interactive capacity with structures such as, for example, substrate-binding regions. These changes are termed "conservative" in the sense that they preserve the structural and, presumably, required functional qualities of the starting molecule. The importance of ICP4 variants is highlighted by the observation, discussed in the examples, that temperature sensitive (ts) mutants of ICP4 exist that are impaired in their ability to transactivate viral genes at elevated temperatures (above about 39° C.), but retain the apoptosis inhibiting function associated with this polypeptide. Further exploration of this dichotomy should reveal significant information on the regions in which these functions lie. Additional variants of this nature may be screened by any of the functional assays provided in the examples.

It has been shown that the transactivation domain of ICP4 lies between about residues 100 and 200, the DNA-binding domains lies between about residues 300 and 500, the nuclear localization domain lies between about residues 700 and 750 and the transactivation domain lies between about residues 750 and 1298.

Conservative amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as equivalent.

In making such changes, the hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity, particularly where the polypeptide created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have been devoted to the prediction of secondary structure, and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan= Trp (W); Tyrosine=Tyr (Y); Valine=Val (V).

In addition to the peptidyl compounds described herein, the inventors also contemplate that other sterically similar compounds may be formulated to mimic the key portions of the peptide structure, called peptidomimetics. Mimetics are peptide-containing molecules which mimic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of receptor and ligand.

Successful applications of the peptide mimetic concept have thus far focused on mimetics of β-turns within proteins. Likely β-turn structures within ICP4 can be predicted by computer-based algorithms as discussed above. Once the component amino acids of the turn are determined, mimetics can be constructed to achieve a similar spatial orientation of the essential elements of the amino acid side chains, as discussed in Johnson et al., supra.

III. Nucleic Acids Encoding ICP4

Also contemplated by the present invention are nucleic acids encoding ICP4. The gene for ICP4 has been given the designation of α4. Because of the degeneracy of the genetic code, many other nucleic acids also may encode a given ICP4. For example, four different three-base codons encode the amino acids alanine, glycine, proline, threonine and valine, while six different codons encode arginine, leucine and serine. Only methionine and tryptophan are encoded by a single codon. A table of amino acids and the corresponding codons is presented herein for use in such embodiments.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In order to generate any nucleic acid encoding ICP4, one need only refer to the preceding codon table. Substitution of the natural codon with any codon encoding the same amino acid will result in a distinct nucleic acid that encodes ICP4. As a practical matter, this can be accomplished by site-directed mutagenesis of an existing α4 gene or de novo chemical synthesis of one or more nucleic acids.

The preceding observations regarding codon selection, site-directed mutagenesis and chemical synthesis apply with equal force to the discussion of substitutional mutants in the section of peptides. Normally, substitutional mutants are generated by site-directed changes in the nucleic acid designed to alter one or more codons of the coding sequence.

In order to express an ICP4 polypeptide, or an antisense α4 transcript, it is necessary to provide an α4 gene in an expression vehicle. The appropriate nucleic acid can be inserted into an expression vector by standard subcloning techniques. For example, an *E. coli* or baculovirus expression vector is used to produce recombinant polypeptide in vitro. The manipulation of these vectors is well known in the art. In one embodiment, the protein is expressed as a fusion protein with β-gal, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these fusion systems produce recombinant protein bearing only a small number of additional amino acids, which are unlikely to affect the functional capacity of the recombinant protein. For example, both the FLAG system and the 6x His system add only short sequences, both of which are known to be poorly antigenic and which do not adversely affect folding of the protein to its native conformation. Other fusion systems produce proteins where it is desirable to excise the fusion partner from the desired protein. In another embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example E. coli, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g 8M) or chaotropic agents such as guanidine hydrochloride in the presence of reducing agents such as β-mercaptoethanol or DTT (dithiothreitol).

Under some circumstances, it may be advantageous to incubate the polypeptide for several hours under conditions suitable for the protein to undergo a refolding process into a conformation which more closely resembles that of the native protein. Such conditions generally include low protein concentrations less than 500 μg/ml, low levels of reducing agent, concentrations of urea less than 2M and often the presence of reagents such as a mixture of reduced and oxidized glutathione which facilitate the interchange of disulphide bonds within the protein molecule.

The refolding process can be monitored, for example, by SDS-PAGE or with antibodies which are specific for the native molecule (which can be obtained from animals vaccinated with the native molecule isolated from parasites). Following refolding, the protein can then be purified further and separated from the refolding mixture by chromatography on any of several supports including ion exchange resins, gel permeation resins or on a variety of affinity columns.

In yet another embodiment, the expression system used is one driven by the baculovirus polyhedron promoter. The gene encoding the protein can be manipulated by standard techniques in order to facilitate cloning into the baculovirus vector. A preferred baculovirus vector is the pBlueBac vector (Invitrogen, Sorrento, Calif.). The vector carrying the α4 gene is transfected into *Spodoptera frugiperda* (Sf9) cells by standard protocols, and the cells are cultured and processed to produce the recombinant protein.

There also are a variety of eukaryotic vectors that provide a suitable vehicle in which recombinant ICP4 can be produced. HSV itself has been used in tissue culture to express a large number of exogenous genes as well as for high level expression of its endogenous genes. For example, the chicken ovalbumin gene has been expressed from HSV using an α promoter. Herz and Roizman (1983). The lacZ gene also has been expressed under a variety of HSV promoters.

In an alternative embodiment, the α4 nucleic acids employed may actually encode antisense constructs that hybridize, under intracellular conditions, to an α4 nucleic acid. The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a nonhomologous region (e.g., a ribozyme) could be designed. These molecules, though having less than 50% homology, would bind to target sequences under appropriate conditions.

While all or part of the α4 gene sequence may be employed in the context of antisense construction, short oligonucleotides are easier to make and increase in vivo accessibility. However, both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the α4 promoter. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 2 and 3 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $\alpha_{1\text{-Antitrypsin}}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |

TABLE 2-continued

| PROMOTER |
| --- |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |

Use of the baculovirus system will involve high level expression from the powerful polyhedron promoter.

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In various embodiments of the invention, the expression construct may comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

In a preferred embodiment, the vector is HSV. Because HSV is neurotropic, it has generated considerable interest in treating nervous system disorders. Moreover, the ability of HSV to establish latent infections in non-dividing neuronal cells without integrating in to the host cell chromosome or otherwise altering the host cell's metabolism, along with the existence of a promoter that is active during latency. And though much attention has focused on the neurotropic applications of HSV, this vector also can be exploited for other tissues.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al., 1995.

IV. Methods for Screening

A. Inhibitors of ICP4 Anti-Apoptotic Activity

In one embodiment of the present invention, there are provided methods of screening compounds for activity against ICP4's anti-apoptotic activity. These screening methods will determine the cell pathology of target cells that express ICP4, both in the presence and absence of the test compound. At least three different assays may be employed, as discussed below.

First, one may look at DNA fragmentation using a separative method, e.g., chromatography or electrophoresis, to size fractionate the sample. As described in greater detail in the examples, an exemplary assay involves the isolation of DNA from cells, followed by agarose gel electrophoresis and staining with ethidium bromide. DNA fragmentation, characteristic of apoptosis, will be visualized as "ladders" containing a wide range of fragment sizes.

Second, one may employ terminal deoxynucleotidyl transferase mediated dUTP-biotin nick end labeling (TUNEL) assays to measures the integrity of DNA (Gorczyca, 1993). This assay measures the fragmentation of DNA by monitoring the incorporation of labeled UTP into broken DNA strands by the enzyme terminal transferase. The incorporation can be monitored by electroscopy or by cell sorting methodologies (e.g., FACS)

Third, one may examine cells using standard light or electron microscopy to assess the presence or absence of the cytopathologies characteristic of apoptosis. Those of skill in the art, applying standard methods of microscopy, will be able to assess cytopathology.

In each of these assays, a cell will be employed as the target for induction and inhibition of apoptosis. In one embodiment, the cell will be infected with HSV that expresses its own ICP4 protein. In a second embodiment, the cell will carry the α4 gene linked to a viral promoter. Infection with the appropriate virus will result in stimulation of the α4 gene and expression of ICP4. In these first two embodiments, the infection should induce apoptosis in the cell, and the expression of ICP4 should limit this effect. In a third embodiment, the cell will contain, as part of its own genetic material, an inducible version of the ICP4 gene (i.e., α4 linked to an inducible promoter). In this situation, it will be necessary to induce apoptosis via some other mechanism, such as hypothermia, and express ICP4 by inducing the promoter.

The cell is contacted with a candidate inhibitor substance in order to assess its effect on ICP4 activity. The substance may be contacted with the cell prior to, at the same time, or after the provision of ICP4. In some cases, the candidate inhibitor substance may be contacted with the cell directly. In other situations, depending on the nature and putative mechanism of action, the candidate inhibitor substance may be reformulated to provide improved uptake. For example, where antisense oligonucleotides are provided, these may advantageously be formulated in liposomes or as virally-encapsulated expression vehicles. Where polypeptides are to be tested, it may be advantageous to provide expression vectors encoding these molecules rather than the polypeptides themselves. Essentially, the most reasonable mechanism for delivering an effective amount of the candidate inhibitor substance to the proper intracellular site will be chosen. "Effective amount," for the purposes of the screening assay, is intended to mean an amount that will cause a detectable difference, and preferably a significant difference, in the cytopathology of the cell as compared to a similar treatment of the cell without the candidate inhibitor substance.

Once the candidate inhibitor substance has been provided to a cell that expresses ICP4, the evaluation of cytopathology may be undertaken. Depending on the type of assay used to examine cytopathology, it is possible to automate this process and test hundreds of candidates at the same time. For example, 96-well trays may be employed in which several wells are reserved for controls while the remainder comprise test substances, usually with each substance being tested at several different amounts.

V. Methods for the Inhibition of Apoptosis

In one embodiment of the present invention, there are provided methods for the inhibition of apoptosis in a cell. This is particularly useful where one seeks to immortalize a cell or, at a minimum, increase the longevity of a cell. This permits one to maintain that cell in culture for extended periods of time, perhaps indefinitely. Immortalized cells are useful primarily as factories for production of viral vectors or proteins of interest, but it also may be important to immortalize cell simply so that they may be studied in vitro with greater ease. In addition, though many viruses provide promise as gene therapeutic vectors, these vectors may trigger apoptosis in the cells they infect. Blocking virally-induced apoptosis will prevent cell death caused by these therapeutic vectors. As mentioned above, adenovirus, papilloma viruses, retrovirus, adeno-associated virus and HSV, for example, are candidate gene therapeutic vectors that could benefit from this application.

The general approach to inhibiting apoptosis, according to the present invention, will be to provide a cell with an ICP4 polypeptide, thereby permitting the inhibitory activity of ICP4 to take effect. While it is conceivable that the protein may be delivered directly, a preferred embodiment involves providing a nucleic acid encoding an ICP4 polypeptide, i.e., an α4 gene, to the cell. Following this provision, the ICP4 polypeptide is synthesized by the host cell's transcriptional and translational machinery, as well as any that may be provided by the expression construct. Cisacting regulatory elements necessary to support the expression of the α4 gene will be provided, as described above, in the form of an expression construct. It also is possible that, in the case of an HSV-infected cell, expression of the virally-encoded α4 could be stimulated or enhanced, or the expressed polypeptide stabilized, thereby achieving the same or similar effect.

In order to effect expression of constructs encoding α4 genes, the expression construct must be delivered into a cell. As described above in the discussion of viral vectors, one mechanism for delivery is via viral infection, where the expression construct is encapsidated in a viral particle which will deliver either a replicating or non-replicating nucleic acid. The preferred embodiment is an HSV vector, although virtually any vector would suffice. Similarly, where viral vectors are used to delivery other therapeutic genes, inclusion in these vectors of an α4 gene advantageously will protect the cell from virally induced apoptosis.

Several non-viral methods for the transfer of expression constructs into cultured mammalian cells also are contemplated by the present invention. These include calcium phosphate precipitation (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et. al., 1990), and receptor-mediated transfection (Wu and Wu, 1987; Wu and Wu, 1988). Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well. Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

Other expression constructs which can be employed to deliver a nucleic acid encoding an α4 transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994). Mannose can be used to target the mannose receptor on liver cells. Also, antibodies to CD5 (CLL), CD22 (lymphoma), CD25 (T-cell leukemia) and MAA (melanoma) can similarly be used as targeting moieties. In other embodiments, the delivery vehicle may comprise a ligand and a liposome.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, 3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

VI. Methods for the Induction of Apoptosis

In another embodiment of the present invention, there is contemplated the method of inducing apoptosis in HSV-infected cells, i.e., blocking the function of ICP4. In this way, it may be possible to curtail viral infection by bringing about a premature death of the infected cell. In addition, it may prove effective to use this sort of therapeutic intervention in combination with more traditional chemotherapies, such as the administration acyclovir.

The general form that this aspect of the invention will take is the provision, to a cell, of an agent that will inhibit ICP4 function. Four such agents are contemplated. First, one may employ an antisense nucleic acid that will hybridize either to the α4 gene or the α4 transcript, thereby preventing transcription or translation, respectively. The considerations relevant to the design of antisense constructs have been presented above. Second, one may utilize an ICP4-binding protein or peptide, for example, a peptidomimetic or an antibody that binds immunologically to an ICP4, the binding of either will block or reduce the activity of an ICP4. The methods of making and selecting peptide binding partners and antibodies are well known to those of skill in the art. Third, one may provide to the cell an antagonist of ICP4, for example, the transactivation target sequence, alone or coupled to another agent. And fourth, one may provide an agent that binds to the ICP4 target without the same functional result as would arise with ICP4 binding.

Provision of an α4 gene, an ICP4-binding protein, or an ICP4 antagonist, would be according to any appropriate pharmaceutical route. The formulation of such compositions and their delivery to tissues is discussed below. The method by which the nucleic acid, protein or chemical is transferred, along with the preferred delivery route, will be selected based on the particular site to be treated. Those of skill in the art are capable of determining the most appropriate methods based on the relevant clinical considerations.

Many of the gene transfer techniques that generally are applied in vitro can be adapted for ex vivo or in vivo use. For example, selected organs including the liver, skin, and muscle tissue of rats and mice have been bombarded in vivo (Yang et al., 1990; Zelenin et al., 1991). Naked DNA also has been used in clinical settings to effect gene therapy. These approaches may require surgical exposure of the tumor tissue or direct intratumoral injection. Nicolau et al. (1987) accomplished successful liposome-mediated gene transfer in rats after intravenous injection.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus, it is envisioned that DNA encoding an antisense construct also may be transferred in a similar manner in vivo.

Where the embodiment involves the use of an antibody that recognizes an ICP4 polypeptide, consideration must be given to the mechanism by which the antibody is introduced into the cell cytoplasm. This can be accomplished, for example, by providing an expression construct that encodes a single-chain antibody version of the antibody to be provided. Most of the discussion above relating to expression constructs for antisense versions of α4 genes will be relevant to this aspect of the invention. Alternatively, it is possible to present a bifunctional antibody, where one antigen binding arm of the antibody recognizes an ICP4 polypeptide and the other antigen binding arm recognizes a receptor on the surface of the cell to be targeted. Examples of suitable receptors would be an HSV glycoprotein such as gB, gC, gD, or gH. In addition, it may be possible to exploit the Fc-binding function associated with HSV gE, thereby obviating the need to sacrifice one arm of the antibody for purposes of cell targeting.

Advantageously, one may combine this approach with more conventional chemotherapeutic options. Acyclovir is an active agent against HSV-1 and HSV-2. The drug inhibits actively replicating herpes virus but is not active against latent virus. Acyclovir is available in three formulations. For topical use, a five percent ointment produces therapeutic drug levels in mucocutaneous lesions. For systemic use, acyclovir may be administered orally or intravenously. The usual intravenous dosage in adults with normal renal function is 5 mg/kg infused at a constant rate over one hour and given every eight hours; this dosage produces peak plasma levels at about 10 g/ml. For HSV encephalitis, twice this dose is used. The usual adult oral dosage is 200 mg, five times daily, which produces plasma levels that are less than 10% as high as those achieved with intravenous administration; even these levels are inhibitory to the virus, however. Acyclovir is given in an oral dosage of 800 mg five times daily for the treatment of herpes zoster, although oral administration generally is reserved for patients with severe symptoms. A three percent opthalmic preparation produces inhibitory drug levels in the aqueous humor and is effective for herpes keratitis.

VII. Methods for the Inhibition of Virus-Induced Cell Death In Vivo

In another embodiment of the present invention, there are provided methods for the inhibition of cell death induced in vivo by any cause comprising the provision of ICP4 polypeptides or α4 genes. Also contemplated in this aspect of the invention is the stimulation of viral ICP4 expression, or stabilization of the virally-expressed ICP4 polypeptide. Though inhibition of apoptosis generally is thought of as advantageous to the virus, it may be desirable to effect this result as part of a method of treating a viral infection. For example, if the host cell remains viable, the virus may continue to replicate; alternatively, if apoptosis were occurring, the virus might be inclined to "go latent" in the neural ganglia, where chemotherapeutic intervention is not helpful. Thus, by preventing early death of the cell, ICP4 may cause the virus to remain susceptible to treatment where it otherwise would escape.

The mechanisms for delivering ICP4 proteins and nucleic acids to a cell are discussed elsewhere in this document and need not be repeated here. The use of standard chemotherapeutics has been presented in the preceding section, and is incorporated in this section.

VIII. Pharmaceuticals and In vivo Methods for the Treatment of Disease

Aqueous pharmaceutical compositions of the present invention will have an effective amount of an α4 expression construct, an antisense α4 expression construct, an expression construct that encodes a therapeutic gene along with α4, a protein that inhibits ICP4 function, such as an anti-ICP4 antibody, or an ICP4 polypeptide. Such compositions generally will be dissolved or dispersed in a pharmaceutically acceptable carrier or aqueous medium. An "effective amount," for the purposes of therapy, is defined at that amount that causes a clinically measurable difference in the condition of the subject. This amount will vary depending on the substance, the condition of the patient, the type of treatment, the location of the lesion, etc.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antiftugal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration;

time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains glycosylceramide synthesis inhibitory compounds alone or in combination with a chemotherapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas. In certain other cases, the formulation will be geared for administration to the central nervous system, e.g., the brain.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

IX. Examples

The following examples are included to demonstrate preferred embodiments of the present invention. It should be appreciated by those of skill in the art that that techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar results without departing from the spirit and scope of the invention.

EXAMPLE 1

MATERIALS AND METHODS

Cells. Vero cells were originally obtained from J. McCleland. HSV-1(F) is the prototype HSV-1 strain used in this study (Ejercito et al., 1968). E5, obtained from N. DeLuca of the University of Pittsburgh, is a Vero cell line expressing ICP4 under its own promoter (DeLuca et al., 1985). Expression of ICP4 is transactivated by the infecting virus.

Viruses. HSV-1(F), the prototype HSV-1 strain used in this study, like most wild-type isolates with a history of limited cell culture passages, carries a temperature-sensitive mutation in ICP4 (Ejercito et al., 1968). At the nonpernissive temperature (39.5° C.) it is defective in the expression of β and γ genes. The HSV-1 mutant d120 (obtained from N.

DeLuca) carries a deletion in both copies of the ICP4 gene, and can grow only in cell lines that express ICP4 (DeLuca et al., 1985). The HSV-1 tsHA1 carries a temperature-sensitive mutation in ICP8, a protein essential for viral DNA replication (Conley et al., 1981). At the nonpermissive temperature (39.5° C.) it is defective in DNA synthesis and does not express $\gamma_2$ genes dependent on viral DNA synthesis for their expression. A schematic representation of the genome of HSV-1 is shown in FIG. 1.

Electron photomicroscopy. Vero cells infected with HSV-1(F) or d120 were incubated for 20 hrs at 37° C. Cells were fixed in 2% glutaraldehyde in PBS for 60 min at 4° C., post-fixed with 1% osmium tetroxide, en bloc stained with uranyl acetate (5 mg/ml), dehydrated in acetone, and embedded in Epon 812. Thin sections were examined either unstained or poststained with uranyl acetate and lead hydroxide. The cells were photographed at 6000× in a Siemens 101 electron microscope.

Light photomicroscopy. Cells were labeled with biotinylated dUTP. At indicated times the cells were fixed in ice-cold methanol at −20° C. and air-dried, then rinsed in phosphate buffered saline, reacted for 15 min at room temperature with 40 ml of a solution containing 1× terminal transferase buffer (Promega), 1 mM $CoCl_2$, 0.05 mg/ml bovine serum albumin (BSA), 0.5 nmoles biotin-16-dUTP (Boehringer Mannheim Biochemicals) and 3 units of terminal transferase (TdT, Promega), rinsed extensively in PBS, reacted for 30 min at room temperature with 40 ml of a solution containing Texas red-conjugated avidin in 4× SSC (1× SSC is 0.15M NaCl, 0.015M Na-citrate), 0.1% Triton X-100, 5% (w/v) nonfat dry milk, extensively rinsed with PBS, mounted in 10% PBS in glycerol and examined under a Zeiss confocal fluorescence microscope. The images were captured under identical settings with the software provided by Zeiss and printed in a Tektronix 440 phaser printer. Cells were mock infected, 37° C., 20 hrs; infected with d120 virus, 37° C. 20 hrs; infected with HSV-1(F), 37° C., 20 hrs; infected with d120 virus, 37° C. 30 hrs; mock-infected, 39.5° C., 30 hrs.; infected with d120 virus, 39.5° C., 30 hrs.; and infected with HSV-1(F), 39.5° C., 30 hrs.

DNA Fragmentation Assay. Vero cells or E5 cells were infected with HSV-1(F), d120 mutant, or HSV-1 tsHA1 mutant and maintained at 37° C. or 39.5° C. in the absence or in the presence of phosphonoacetic acid. At 30 hrs after infection, 2×10$^6$ cells per sample were collected, washed in PBS, lysed in a solution containing 10 mM Tris-HCl, pH 8.0, 10 mM EDTA, and 0.5% Triton X-100, and centrifuged at 12,000 rpm for 25 min in an Eppendorf microcentrifuge to pellet chromosomal DNA. Supernatant fluids were digested with 0.1 mg RNase A per ml at 37° C. for 1 hr, for 2 hrs with 1 mg proteinase K per ml at 50° C. in the presence of 1% sodium dodecylsulphate (SDS), extracted with phenol and chloroform, and precipitated in cold ethanol and subjected to electrophoresis on horizontal 1.5% agarose gels containing 5 mg of ethidium bromide per ml. DNA was visualized by UV light transillumination. Photographs were taken with the aid of a computer-assisted image processor (Eagle Eye II, Stratagene).

EXAMPLE 2

RESULTS

An HSV-1 mutant deleted in ICP4 induces apoptosis. In the first series of studies, Vero cells infected with wild-type or the d120 mutant were examined for morphologic evidence of apoptosis. Vero cells were fixed and harvested at 20 to 24 hrs after infection with wild-type or d120, embedded, sectioned, and examined in a Siemens 101 electron microscope. The cells infected with wild-type virus showed typical infected cell morphology, i.e., marginated chromatin, separation of inner and outer nuclear membranes, and accumulation of virus particles in some but not all cells. Cells infected with the d120 deletion mutant exhibited extensive condensation of chromatin, obliteration of the nuclear membrane, and extensive vacuolization and blebbing of the cytoplasm. It was estimated that approximately 40 to 50% of the infected cells exhibited some or all of the morphologic changes described above.

In the second series of studies, Vero cells were mock-infected or infected with 10 PFU of either the wild-type or the d120 mutant virus per cell. After 20 hrs of incubation at 37° C. the cells were fixed, labeled with biotinylated dUTP in the presence of terminal transferase, and then reacted with fluorescent avidin. Mock-infected cells or cells infected with wild-type virus showed no sign of labeling with biotinylated dUTP by terminal transferase, whereas cells infected with d120 and maintained at the same temperature showed extensive fluorescence due to the reaction of fluorescent avidin to biotinylated dUTP incorporated at the DNA termini created by the cleavage of DNA.

In the third series of studies, replicate Vero cell cultures were infected with 10 PFU of either HSV-1(F) or d120 per cell and incubated at 37° C. The study also included a Vero cell culture infected with HSV-1(F), overlaid with medium containing 300 μg of phosphonoacetate per ml and incubated at 37° C., and a set of Vero cell cultures infected with 10 PFU of HSV-1 tsHA1 and incubated at either 37° C. or 39.5° C. This concentration of phosphonoacetate completely inhibits viral DNA synthesis and blocks the expression of $\gamma_2$ genes dependent on viral synthesis for their expression. The cells were harvested at 30 hrs after infection, lysed, and centrifuged to pellet the chromosomal DNA. The supernatant fluids were processed as described above and subjected to electrophoresis in agarose gels to test for the presence of soluble, fragmented DNA.

The results were as follows. Cells infected with d120 deletion mutant yielded high amounts of fragmented DNA which were readily visible on agarose gels stained with ethidium bromide. These ladders were not seen in agarose gels containing electrophoretically separated extracts of wild-type infected cells or E5 cells infected with d120. When Vero cells were incubated in medium containing phosphonoacetate, fragmented DNA was detected from cells infected with d120 mutant but not with the wild-type. Fragmented DNA was visible in extracts of mock-infected cells incubated at 39.5° C., but not in cells infected with HSV-1tsHA1 and incubated at the same temperature.

From this series of studies, it is concluded that (i) HSV-1 is capable of inducing the morphologic and biochemical changes characteristic of apoptosis and these changes are prominent in cells infected with a mutant lacking ICP4; (ii) wild-type virus does not induce apoptosis indicating that ICP4 or a protein expressed subsequently is able to protect cells from apoptosis; (iii) the protective, anti-apoptotic effect is a viral function which does not depend on the onset of viral DNA synthesis; (iv) DNA degradation typical of apoptosis was observed upon incubation at 39.5° C. in mock-infected but not HSV-1tsHA1 infected cells, which suggests that prolonged incubation at the elevated temperature can induce apoptosis that is blocked by a viral function expressed early.

ICP4 expresses an anti-apoptotic function. In a fourth series of studies, Vero or E5 cells were mock infected or infected with 10 PFU per cell with either HSV-1(F) or d120. The cells were incubated at 39.5° C. for 30 hrs. The rationale of these studies was as follows. As noted in Example 1, HSV-1(F) carries a ts lesion in the α4 gene and at the nonpermissive temperature (39.5° C.) expresses only α genes. The α4 gene resident in the E5 cell line and the d120 mutant virus lacking the α4 gene were derived from the HSV-1 (KOS) strain which does not exhibit the ts phenotype. In addition, the α4 gene resident in the E5 cell line is induced after infection and is not expressed in uninfected cells. In the first series of studies, the cells were harvested, lysed, centrifuged to sediment chromosomal DNA and the supernatant fluids were processed as described in Example 1 and subjected to electrophoresis in agarose gels.

The results were as follows. Fragmented DNA was present in lanes containing electrophoretically separated extracts of mock-infected Vero cells, Vero cells infected with d120 mutant, and the mock infected E5 cells. Fragmented DNA was not detected in Vero cells infected with wild-type virus, or in E5 cells infected with either d120 mutant virus or HSV-1(F) virus.

In the second series of studies Vero cells were mock infected, or infected with either d120 or with wild-type virus. After 30 hrs of incubation at 39.5° C., the cells were fixed and labeled with biotinylated dUTP by terminal transferase, and reacted with fluorescent avidin. Fluorescence was detected in mock-infected or infected with d120 mutant, but not in cells infected with wild-type virus.

These studies allowed permit the conclusion conclude that HSV-1(F) α4 gene encodes a function which blocks apoptosis reflected in the degradation of DNA, and that this function is separable from the repressor and transactivator functions of ICP4 which are affected by the temperature sensitive lesion of the α4 gene of HSV-1 (F).

A summary of the results is provided in Table 4. Induction of (+), or protection from (−) apoptosis is indicated upon conditions (infecting virus and incubation temperature) which induce apoptosis in Vero and E5 cell lines. "nt" indicates not tested.

TABLE 4

|  | VERO (37° C.) | VERO (39° C.) | E5 (37° C.) | E5 (39.5° C.) |
|---|---|---|---|---|
| MOCK | − | + | − | + |
| HSV-1(F) | − | − | − | − |
| HSV-1 d120 | + | + | − | − |
| HSV-1 tsHA1 | − | − | nt | nt |

X. References

The following references, to the extent that they provide exemplary procedural details or other information supplementary to that set forth herein, are incorporated by reference:

Baichwal and Sugden, In: *GENE TRANSFER* Kucherlapati, R., ed. New York: Plenum Press, pp. 117–148, 1986.
Batterson & Roizman, *J. Virol*, 46:371–377, 1983.
Benvenisty & Neshif, *Proc. Nat'l Acad Sci. USA* 83:9551–9555, 1986.
Bittner et al., *Methods in Enzymol.*, 153:516–544, 1987.
Brutlag et al., *CABIOS*, 6:237–245, 1990.
Campbell et al., *J. Mol. Biol.*, 180:1–19, 1984.
Chen and Okayama, *Mol. Cell Biol.*, 7:2745–2752, 1987.
Chou and Fasman, *Adv. Enzymol. Relat. Areas Mol. Biol.* 47:45–148, 1978a.
Chou and Fasman, *Ann. Rev. Biochem.* 47:251–276, 1978b.
Chou and Fasman, *Biochemistry*, 13(2):211–222, 1974b.
Chou and Fasman, *Biochemistry*, 13(2):222–245, 1974a.
Chou and Fasman, *Biophys. J.*, 26:367–384, 1979.
Chou and Roizman, *Proc. Nat'l Acad Sci. USA*, 89:3266–3270, 1992.
Clem & Miller, In Apoptosis II: The Molecular Basis of Apoptosis in Disease, L. D. Tomei and F. O. Cope, eds. (Cold Spring Harbor Laboratory Press), pp. 89–110, 1994a.
Conley et al., *J. Virol.*, 37:191–206, 1981.
DeLuca et al., *J. Virol.*, 56:558–570, 1985.
Dixon & Shaffer, *J. Virol.*, 36:189–203, 1980.
Dubensky et al., Proc. Nat'l Acad. Sci. USA, 81:7529–7533, 1984.
Ejercito et al., *J. Gen. Virol.*, 2:357–364, 1968.
Faber & Wilcox, *Nucleic Acids Res.*, 14:6067–6083, 1986.
Fechheimer et al., *Proc. Nat'l Acad. Sci. USA*, 84:8463–8467, 1987.
Ferkol et al., *FASEB J.*, 7:1081–1091, 1993.
Fetrow & Bryant, *Biotechnology*, 11:479–483, 1993.
Fraley et al., Proc. Nat'l Acad Sci. USA, 76:3348–3352, 1979.
Freshner, "Animal Cell Culture: A Practical Approach," Second Edition, Oxford/New York, IRL Press, Oxford University Press, 1992.
Ghosh and Bachhawat, In: Wu G. and C. Wu ed. Liver diseases, targeted diagnosis and therapy using specific receptors and ligands. New York: Marcel Dekker, pp. 87–104, 1991.
Glorioso et al., *Ann. Rev. Microbiol.* 49:675–710, 1995.
Gopal, *Mol. Cell Biol.*, 5:1188–1190, 1985.
Gorczyca et al, *Cancer Res.*, 53:1945–1951, 1993.
Graham and Van Der Eb, *Virology*, 52:456–467, 1973.
Harland and Weintraub, *J. Cell Biol.*, 101:1094–1099, 1985.
Henderson et al., Proc. Nat'l Acad. Sci. USA, 90:8479–8483, 1993.
Herz and Roizinan, *Cell*, 33:145–151, 1983.
Holland et al., *Virology*, 101:10–18, 1980.
Honess & Roizman, *J. Virol.*, 14:8–19, 1974.
Honess & Roizman, *J. Virol.*, 16:1308–1326, 1975.
Jameson and Wolf, *Comput. Appl. Biosci.*, 4(1):181–186, 1988.
Johnson et al., *BIOTECHNOLOGY AND PHARMACY*, Pezzuto et al., eds., Chapman and Hall, New York, 1993.
Kaneda et al., *Science*, 243:375–378, 1989.
Kato et al., *J. Biol. Chem.*, 266:3361–3364, 1991.
Klein et al., *Nature*, 327:70–73, 1987.
Kristie & Roizman, *Proc. Nat'l Acad Sci. USA*, 83:3218–3222, 1986a.
Kristie & Roizman, *Proc. Nat'l Acad Sci USA*, 83:4700–4704, 1986b.
Kuddus et al., *J. Virol.*, 69:5568–5575, 1995.
Kyte and Doolittle, *J. Mol. Biol.*, 157(1):105–132, 1982.
Leopardi et al., *J. Virol.*, 69:3042–3048, 1995.
McCarthy et al., *Proc. Nat'l Acad. Sci. USA*, 91:3979–83, 1994.
Michael & Roizman, *Proc. Nat'l Acad. Sci. USA*, 86:9808–9812, 1989.
Michael & Roizman, *Proc. Nat'l Acad. Sci. USA*, 90:2286–2290, 1993.
Michael et al., *Science*, 239:1531–1534, 1988.
Mizrahi, *Process Biochem.*, (August):9–12, 1983.
Muller, M. T., *J. Virol.*, 61:858–865, 1987.
Nicolas and Rubenstein, In: *Vectors: A survey of molecular cloning vectors and their uses*, Rodriguez and Denhardt (eds.), Stoneham: Butterworth, pp. 494–513, 1988.
Nicolau and Sene, *Biochem. Biophys. Acta*, 721:185–190, 1982.

Nicolau et al., *Methods Enzymol*, 149:157–176, 1987.
Pan and Griep, *Genes Dev.*, 8:1285–99, 1994.
Perales et al., *Proc. Nat'l Acad Sci. USA*, 91:4086–4090, 1994.
Phillips et al., In: *Large Scale Mammalian Cell Culture* (Feder, J. and Tolbert, W. R., eds.), Academic Press, Orlando, Fla., U.S.A., 1985.
Post et al., *Cell* 24:555–565, 1981.
Potter et al., *Proc. Nat'l Acad. Sci. USA*, 81:7161–7165, 1984.
Rao et al. Proc. Nat'l Acad. Sci. USA, 89:7742–7746, 1992.
Ray et al., *Cell*, 69:597–604, 1992.
Ridgeway, In. Rodriguez R L, Denhardt D T, ed. Vectors: A survey of molecular cloning vectors and their uses. Stoneham: Butterworth, pp. 467–492, 1988.
Rippe et al., *Mol. Cell Biol*, 10:689–695, 1990.
Roizrnan & Sears, In Fields' Virology, 3rd Edition, eds. Fields, et al. (Raven Press, New York, N.Y.), pp. 2231–2295, 1995.
Sarre, T. F., *Byosistems*, 22:311–325, 1989.
Shen and Shenk, *Curr. Opin. Genet. Dev.*, 5:105–111, 1995.
Shepard & DeLuca, *J. Virol.*, 65:787–795, 1991.
Temin, In: *Gene Transfer*, Kucherlapati (ed.), New York: Plenum Press, pp. 149–188, 1986.
Tur-Kaspa et al., *Mol. Cell Biol.*, 6:716–718, 1986.
Wagner et al., *Science*, 260:1510–1513, 1990.
Weinberger et al., *Science*, 228:740–742, 1985.
White & Gooding, *The Molecular Basis of Apoptosis in Disease*, L. D. Tomei and F. O. Cope, eds. (Cold Spring Harbor Laboratory Press), pp. 111–141, 1994.
White, E., *Genes and Dev.*, 7:2277–2284, 1993.
Wolf et al., *Comput. Appl. Biosci.*, 4(1):187–191, 1988.
Wong et al., *Gene*, 10:87–94, 1980.
Wu and Wu, *Adv. Drug Delivery Rev.*, 12:159–167,1993.
Wu and Wu, *Biochemistry*, 27:887–892, 1988.
Wu and Wu, *J. Biol. Chem*, 262:4429–4432, 1987.
Wyllie et al., *Int. Rev. Cytol.*, 68:251–306, 1980.
Yang et al., *Proc. Nat'l Acad. Sci. USA*, 87:9568–9572, 1990.
Zelenin et al., *FEBS Lett.*, 280:94–96, 1991.
Zhu et al., *J. Virol.*, 69:7960–7970, 1995.

What is claimed is:

1. A screening method for compounds having inhibitory activity against HSV ICP4 polypeptide-induced inhibition of apoptosis comprising the steps of:
   (a) providing a first cell comprising an HSV α4 gene under the control of an HSV immediate early promoter;
   (b) infecting said first cell with a herpes simplex virus that lacks a functional α4 gene;
   (c) contacting said first cell with a test compound;
   (d) incubating said first cell under conditions permitting viral replication; and
   (e) comparing the cell pathology of said first cell following incubation with (i) the cell pathology of a second cell that lacks an HSV α4 gene following infection with said herpes simplex virus and (ii) the cell pathology of a third cell comprising an HSV α4 gene under the control of an HSV immediate early promoter following infection with said herpes simplex virus but in the absence of said test compound.

2. The method of claim 1, wherein said cell pathology comprises condensation of chromatin, obliteration of nuclear membranes, vacuolization, cytoplasmic blebbing and DNA fragmentation.

3. The method of claim 1, wherein said first cell contains a wild-type HSV α4 gene under the control of an α4 promoter integrated into the genome of said first cell.

4. The method of claim 3, wherein said herpes simplex virus that lacks a functional HSV α4 gene has a deletion in both copies of the virally-encoded α4 genes.

5. A screening method for compounds having inhibitory activity against HSV ICP4 polypeptide-induced inhibition of apoptosis comprising the steps of:
   (a) providing a first cell comprising an HSV α4 gene under the control of an HSV immediate early promoter;
   (b) infecting said first cell with a herpes simplex virus that contains a conditionally defective α4 gene;
   (c) contacting said first cell with a test compound;
   (d) incubating said first cell under conditions permitting viral replication but resulting in the production of defective α4 gene product; and
   (e) comparing the cell pathology of said first cell following incubation with (i) the cell pathology of a second cell that lacks an HSV α4 gene following infection with said herpes simplex virus and (ii) the cell pathology of a third cell comprising an HSV α4 gene under the control of an HSV immediate early promoter following infection with said herpes simplex virus but in the absence of said test compound.

6. The method of claim 5, wherein said herpes simplex virus that lacks a functional HSV α4 gene carries a temperature sensitive mutation in both copies of the virally-encoded α4 gene and the incubation is at 39.5° C.

7. The method of claim 5, wherein said cell pathology comprises condensation of chromatin, obliteration of nuclear membranes, vacuolization, cytoplasmic blebbing and DNA fragmentation.

8. The method of claim 5, wherein said first cell contains a wild-type HSV α4 gene under the control of an α4 promoter integrated into the genome of said first cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4257 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GCTGCTCCTC  CTTCCCGCCG  GCCCCTGGGA  CTATATGAGC  CCGAGGACGC  CCCGATCGTC      60

CACACGGAGC  GCGGCTGCCG  ACACGGATCC  ACGACCCGAC  GCGGGACCGC  CAGAGACAGA     120

CCGTCAGACG  CTCGCCGCGC  CGGGACGCCG  ATACGCGGAC  GAAGCGCGGG  AGGGGGATCG     180

GCCGTCCCTG  TCCTTTTTCC  CACCCAAGCA  TCGACCGGTC  CGCGCTAGTT  CCGCGTCGAC     240

GGCGGGGGTC  GTCGGGGTCC  GTGGGTCTCG  CCCCCTCCCC  CCATCGAGAG  TCCGTAGGTG     300

ACCTACCGTG  CTACGTCCGC  CGTCGCAGCC  GTATCCCCGG  AGGATCGCCC  CGCATCGGCG     360

ATGGCGTCGG  AGAACAAGCA  GCGCCCCGGC  TCCCCGGGCC  CCACCGACGG  GCCGCCGCCC     420

ACCCCGAGCC  CAGACCGCGA  CGAGCGGGGG  GCCCTCGGGT  GGGGCGCGGA  GACGGAGGAG     480

GGCGGGGACG  ACCCCGACCA  CGACCCCGAC  CACCCCACG   ACCTCGACGA  CGCCCGGCGG     540

GACGGGAGGG  CCCCCGCGGC  GGGCACCGAC  GCCGGCGAGG  ACGCCGGGGA  CGCCGTCTCG     600

CCGCGACAGC  TGGCTCTGCT  GGCCTCCATG  GTAGAGGAGG  CCGTCCGGAC  GATCCCGACG     660

CCCGACCCCG  CGGCCTCGCC  GCCCCGGACC  CCCGCCTTTC  GAGCCGACGA  CGATGACGGG     720

GACGAGTACG  ACGACGCAGC  CGACGCCGCC  GGCGACCGGG  CCCCGGCCCG  GGGCCGCGAA     780

CGGGAGGCCC  CGCTACGCGG  CGCGTATCCG  GACCCCACGG  ACCGCCTGTC  GCCGCGCCCG     840

CCGGCCCAGC  CGCCGCGGAG  ACGTCGTCAC  GGCCGGTGGC  GGCCATCGGC  GTCATCGACC     900

TCGTCGGACT  CCGGGTCCTC  GTCCTCGTCG  TCCGCATCCT  CTTCGTCCTC  GTCGTCCGAC     960

GAGGACGAGG  ACGACGACGG  CAACGACGCG  GCCGACCACG  CACGCGAGGC  GCGGGCCGTC    1020

GGGCGGGGTC  CGTCGAGCGC  GGCGCCGGCA  GCCCCCGGGC  GGACGCCGCC  CCCGCCCGGG    1080
```

-continued

| | | | | | |
|---|---|---|---|---|---|
| CCACCCCCCC | TCTCCGAGGC | CGCGCCCAAG | CCCCGGGCGG | CGGCGAGGAC | CCCCGCGGCC | 1140 |
| TCCGCGGGCC | GCATCGAGCG | CCGCCGGGCC | CGCGCGGCGG | TGGCCGGCCG | CGACGCCACG | 1200 |
| GGCCGCTTCA | CGGCCGGGCA | GCCCCGGCGG | GTCGAGCTGG | ACGCCGACGC | GACCTCCGGC | 1260 |
| GCCTTCTACG | CGCGCTATCG | CGACGGGTAC | GTCAGCGGGG | AGCCGTGGCC | CGGCGCCGGG | 1320 |
| CCCCCGCCCC | CGGGGCGGGT | GCTGTACGGC | GGCCTGGGCG | ACAGCCGCCC | GGGCCTCTGG | 1380 |
| GGGGCGCCCG | AGGCGGAGGA | GGCGCGACGC | CGGTTCGAGG | CCTCGGGCGC | CCCGGCGGCC | 1440 |
| GTGTGGGCGC | CCGAGCTGGG | CGACGCCGCG | CAGCAGTACG | CCCTGATCAC | GCGGCTGCTG | 1500 |
| TACACCCCGG | ACGCGGAGGC | CATGGGGTGG | CTCCAGAACC | CGCGCGTGGT | CCCCGGGGAC | 1560 |
| GTGGCGCTGG | ACCAGGCCTG | CTTCCGGATC | TCGGGCGCCG | CGCGCAACAG | CAGCTCCTTC | 1620 |
| ATCACCGGCA | GCGTGGCGCG | GGCCGTGCCC | CACCTGGGCT | ACGCCATGGC | GGCCGGCCGC | 1680 |
| TTCGGCTGGG | GCCTGGCGCA | CGCGGCGGCC | GCCGTGGCCA | TGAGCCGCCG | ATACGACCGC | 1740 |
| GCGCAGAAGG | GCTTCCTGCT | GACCAGCCTG | CGCCGCGCCT | ACGCGCCCCT | GTTGGCGCGC | 1800 |
| GAGAACGCGG | CGCTGACGGG | GGCCGCGGGG | AGCCCCGGCG | CCGGCGCAGA | TGACGAGGGG | 1860 |
| GTCGCCGCCG | TCGCCGCCGC | CGCACCGGGC | GAGCGCGCGG | TGCCCGCCGG | GTACGGCGCC | 1920 |
| GCGGGGATCC | TCGCCGCCCT | GGGGCGGCTG | TCCGCCGCGC | CCGCCTCCCC | CGCGGGGGGC | 1980 |
| GACGACCCCG | ACGCCGCCCG | CCACGCCGAC | GCCGACGACG | ACGCCGGGCG | CCGCGCCCAG | 2040 |
| GCCGGCCGCG | TGGCCGTCGA | GTGCCTGGCC | GCCTGCCGCG | GGATCCTGGA | GGCGCTGGCC | 2100 |
| GAGGGCTTCG | ACGGCGACCT | GGCGGCCGTC | CCGGGGCTGG | CCGGGGCCCG | GCCCGCCAGC | 2160 |
| CCCCCGCGGC | CGGAGGGACC | CGCGGGCCCC | GCTTCCCCGC | CGCCGCCGCA | CGCCGACGCG | 2220 |
| CCCCGCCTGC | GCGCGTGGCT | GCGCGAGCTG | CGGTTCGTGC | GCGACGCGCT | GGTGCTCATG | 2280 |
| CGCCTGCGCG | GGACCTGCG | CGTGGCCGGC | GGCAGCGAGG | CCGCCGTGGC | CGCCGTGCGC | 2340 |
| GCCGTGAGCC | TGGTCGCCGG | GGCCCTGGGC | CCCGCGCTGC | CGCGGGACCC | GCGCCTGCCG | 2400 |
| AGCTCCGCGG | CCGCCGCCGC | CGCGGACCTG | CTGTTTGACA | ACCAGAGCCT | GCGCCCCCTG | 2460 |
| CTGGCGGCGG | CGGCCAGCGC | ACCGGACGCC | GCCGACGCGC | TGGCGGCCGC | CGCCGCCTCC | 2520 |
| GCCGCGCCGC | GGGAGGGGCG | CAAGCGCAAG | AGTCCCGGCC | CGGCCCGGCC | GCCCGGAGGC | 2580 |
| GGCGGCCCGC | GACCCCCGAA | GACGAAGAAG | AGCGGCGCGG | ACGCCCCGG | CTCGGACGCC | 2640 |
| CGCGCCCCCC | TCCCCGCGCC | CGCGCCCCCC | TCCACGCCCC | CGGGCCCGA | GCCCGCCCCC | 2700 |
| GCCCAGCCCG | CGGCGCCCCG | GGCCGCCGCG | GCGCAGGCCC | GCCCGCGCCC | CGTGGCCGTG | 2760 |
| TCGCGCCGGC | CCGCCGAGGG | CCCCGACCCC | CTGGGCGGCT | GGCGGCGGCA | GCCCCGGGG | 2820 |
| CCCAGCCACA | CGGCGGCGCC | CGCGGCCGCC | GCCCTGGAGG | CCTACTGCTC | CCCGCGCGCC | 2880 |
| GTGGCCGAGC | TCACGGACCA | CCCGCTGTTC | CCCGTCCCCT | GGCGACCGGC | CCTCATGTTT | 2940 |
| GACCCGCGGG | CCCTGGCCTC | GATCGCCGCG | CGGTGCGCCG | GCCCGCCCC | CGCCGCCCAG | 3000 |
| GCCGCGTGCG | GCGGCGGCGA | CGACGACGAT | AACCCCCACC | CCCACGGGGC | CGCCGGGGGC | 3060 |
| CGCCTCTTTG | GCCCCCTGCG | CGCCTCGGGC | CCGCTGCGCC | GCATGGCGGC | CTGGATGCGC | 3120 |
| CAGATCCCCG | ACCCCGAGGA | CGTGCGCGTG | GTGGTGCTGT | ACTCGCCGCT | GCCGGGCGAG | 3180 |
| GACCTGGCCG | GCGGCGGGGC | CTCGGGGGGG | CCGCCGGAGT | GGTCCGCCGA | GCGCGGCGGG | 3240 |
| CTGTCCTGCC | TGCTGGCGGC | CCTGGCCAAC | CGGCTGTGCG | GCCGGACAC | GGCCGCCTGG | 3300 |
| GCGGGCAATT | GGACCGGCGC | CCCCGACGTG | TCGGCGCTGG | GCGCACAGGG | CGTGCTGCTG | 3360 |
| CTGTCCACGC | GGGACCTGGC | CTTCGCCGGG | GCCGTGGAGT | TTCTGGGGCT | GCTCGCCAGC | 3420 |
| GCCGGCGACC | GGCGGCTCAT | CGTGGTCAAC | ACCGTGCGCG | CCTGCGACTG | GCCCGCCGAC | 3480 |

| | | | | | |
|---|---|---|---|---|---|
| GGGCCCGCGG | TGTCGCGGCA | GCACGCCTAC | CTGGCGTGCG | AGCTGCTGCC | CGCCGTGCAG 3540 |
| TGCGCCGTGC | GCTGGCCGGC | GGCGCGGGAC | CTGCGCCGCA | CGGTGCTGGC | CTCGGGCCGC 3600 |
| GTGTTCGGCC | CGGGGGTCTT | CGCGCGCGTG | GAGGCCGCGC | ACGCGCGCCT | GTACCCCGAC 3660 |
| GCGCCGCCGC | TGCGCCTGTG | CCGCGGCGGC | AACGTGCGCT | ACCGCGTGCG | CACGCGCTTC 3720 |
| GGCCCGGACA | CGCCGGTGCC | CATGTCCCCG | CGCGAGTACC | GCCGGGCCGT | GCTGCCGGCG 3780 |
| CTGGACGGCC | GGGCGGCGGC | CTCGGGGACC | ACCGACGCCA | TGGCGCCCGG | CGCGCCGGAC 3840 |
| TTCTGCGAGG | AGGAGGCCCA | CTCGCACGCC | GCCTGCGCGC | GCTGGGGCCT | GGGCGCGCCG 3900 |
| CTGCGGCCCG | TGTACGTGGC | GCTGGGGCGC | GAGGCGGTGC | GCGCCGGCCC | GGCCCGGTGG 3960 |
| CGCGGGCCGC | GGAGGGACTT | TTGCGCCCGC | GCCCTGCTGG | AGCCCGACGA | CGACGCCCCC 4020 |
| CCGCTGGTGC | TGCGCGGCGA | CGACGACGGC | CCGGGGGCCC | TGCCGCCGGC | GCCGCCCGGG 4080 |
| ATTCGCTGGG | CCTCGGCCAC | GGGCCGCAGC | GGCACCGTGC | TGGCGGCGGC | GGGGGCCGTG 4140 |
| GAGGTGCTGG | GGGCGGAGGC | GGGCTTGGCC | ACGCCCCGC | GGCGGGAAGT | TGTGGACTGG 4200 |
| GAAGGCGCCT | GGGACGAAGA | CGACGGCGGC | GCGTTCGAGG | GGGACGGGGT | GCTGTAA 4257 |

( 2 ) INFORMATION FOR SEQ ID NO:2:

( i ) SEQUENCE CHARACTERISTICS:
        ( A ) LENGTH: 1298 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met Ala Ser Glu Asn Lys Gln Arg Pro Gly Ser Pro Gly Pro Thr Asp
 1               5                  10                  15

Gly Pro Pro Pro Thr Pro Ser Pro Asp Arg Asp Glu Arg Gly Ala Leu
            20                  25                  30

Gly Trp Gly Ala Glu Thr Glu Glu Gly Gly Asp Asp Pro Asp His Asp
        35                  40                  45

Pro Asp His Pro His Asp Leu Asp Asp Ala Arg Arg Asp Gly Arg Ala
    50                  55                  60

Pro Ala Ala Gly Thr Asp Ala Gly Glu Asp Ala Gly Asp Ala Val Ser
65                  70                  75                  80

Pro Arg Gln Leu Ala Leu Leu Ala Ser Met Val Glu Glu Ala Val Arg
                85                  90                  95

Thr Ile Pro Thr Pro Asp Pro Ala Ala Ser Pro Pro Arg Thr Pro Ala
            100                 105                 110

Phe Arg Ala Asp Asp Asp Asp Gly Asp Glu Tyr Asp Asp Ala Ala Asp
        115                 120                 125

Ala Ala Gly Asp Arg Ala Pro Ala Arg Gly Arg Glu Arg Glu Ala Pro
    130                 135                 140

Leu Arg Gly Ala Tyr Pro Asp Pro Thr Asp Arg Leu Ser Pro Arg Pro
145                 150                 155                 160

Pro Ala Gln Pro Pro Arg Arg Arg Arg His Gly Arg Trp Arg Pro Ser
                165                 170                 175

Ala Ser Ser Thr Ser Ser Asp Ser Gly Ser Ser Ser Ser Ser Ser Ala
            180                 185                 190

Ser Ser Ser Ser Ser Ser Ser Asp Glu Asp Glu Asp Asp Gly Asn
        195                 200                 205

Asp Ala Ala Asp His Ala Arg Glu Ala Arg Ala Val Gly Arg Gly Pro
    210                 215                 220
```

```
Ser  Ser  Ala  Ala  Pro  Ala  Ala  Pro  Gly  Arg  Thr  Pro  Pro  Pro  Gly
225                 230                 235                           240

Pro  Pro  Pro  Leu  Ser  Glu  Ala  Ala  Pro  Lys  Pro  Arg  Ala  Ala  Arg
                    245                 250                           255

Thr  Pro  Ala  Ala  Ser  Ala  Gly  Arg  Ile  Glu  Arg  Arg  Arg  Arg  Ala
               260                 265                      270

Ala  Val  Ala  Gly  Arg  Asp  Ala  Thr  Gly  Arg  Phe  Thr  Ala  Gly  Gln  Pro
          275                 280                      285

Arg  Arg  Val  Glu  Leu  Asp  Ala  Asp  Ala  Thr  Ser  Gly  Ala  Phe  Tyr  Ala
     290                      295                 300

Arg  Tyr  Arg  Asp  Gly  Tyr  Val  Ser  Gly  Glu  Pro  Trp  Pro  Gly  Ala  Gly
305                      310                 315                           320

Pro  Pro  Pro  Pro  Gly  Arg  Val  Leu  Tyr  Gly  Gly  Leu  Gly  Asp  Ser  Arg
                    325                 330                      335

Pro  Gly  Leu  Trp  Gly  Ala  Pro  Glu  Ala  Glu  Ala  Arg  Arg  Arg  Phe
               340                 345                      350

Glu  Ala  Ser  Gly  Ala  Pro  Ala  Ala  Val  Trp  Ala  Pro  Glu  Leu  Gly  Asp
               355                 360                 365

Ala  Ala  Gln  Gln  Tyr  Ala  Leu  Ile  Thr  Arg  Leu  Leu  Tyr  Thr  Pro  Asp
     370                      375                 380

Ala  Glu  Ala  Met  Gly  Trp  Leu  Gln  Asn  Pro  Arg  Val  Val  Pro  Gly  Asp
385                 390                 395                           400

Val  Ala  Leu  Asp  Gln  Ala  Cys  Phe  Arg  Ile  Ser  Gly  Ala  Ala  Arg  Asn
               405                 410                           415

Ser  Ser  Ser  Phe  Ile  Thr  Gly  Ser  Val  Ala  Arg  Ala  Val  Pro  His  Leu
               420                 425                      430

Gly  Tyr  Ala  Met  Ala  Ala  Gly  Arg  Phe  Gly  Trp  Gly  Leu  Ala  His  Ala
               435                 440                      445

Ala  Ala  Ala  Val  Ala  Met  Ser  Arg  Arg  Tyr  Asp  Arg  Ala  Gln  Lys  Gly
     450                      455                 460

Phe  Leu  Leu  Thr  Ser  Leu  Arg  Arg  Ala  Tyr  Ala  Pro  Leu  Leu  Ala  Arg
465                      470                 475                           480

Glu  Asn  Ala  Ala  Leu  Thr  Gly  Ala  Ala  Gly  Ser  Pro  Gly  Ala  Gly  Ala
                    485                 490                           495

Asp  Asp  Glu  Gly  Val  Ala  Ala  Val  Ala  Ala  Ala  Ala  Pro  Gly  Glu  Arg
               500                 505                      510

Ala  Val  Pro  Ala  Gly  Tyr  Gly  Ala  Ala  Gly  Ile  Leu  Ala  Ala  Leu  Gly
          515                 520                 525

Arg  Leu  Ser  Ala  Ala  Pro  Ala  Ser  Pro  Ala  Gly  Gly  Asp  Asp  Pro  Asp
     530                      535                 540

Ala  Ala  Arg  His  Ala  Asp  Ala  Asp  Asp  Ala  Gly  Arg  Arg  Ala  Gln
545                      550                 555                      560

Ala  Gly  Arg  Val  Ala  Val  Glu  Cys  Leu  Ala  Ala  Cys  Arg  Gly  Ile  Leu
               565                 570                      575

Glu  Ala  Leu  Ala  Glu  Gly  Phe  Asp  Gly  Asp  Leu  Ala  Ala  Val  Pro  Gly
               580                 585                      590

Leu  Ala  Gly  Ala  Arg  Pro  Ala  Ser  Pro  Pro  Arg  Pro  Glu  Gly  Pro  Ala
          595                 600                 605

Gly  Pro  Ala  Ser  Pro  Pro  Pro  His  Ala  Asp  Ala  Pro  Arg  Leu  Arg
     610                 615                 620

Ala  Trp  Leu  Arg  Glu  Leu  Arg  Phe  Val  Arg  Asp  Ala  Leu  Val  Leu  Met
625                      630                 635                           640

Arg  Leu  Arg  Gly  Asp  Leu  Arg  Val  Ala  Gly  Gly  Ser  Glu  Ala  Ala  Val
               645                 650                      655
```

-continued

```
Ala  Ala  Val  Arg  Ala  Val  Ser  Leu  Val  Ala  Gly  Ala  Leu  Gly  Pro  Ala
               660                      665                     670

Leu  Pro  Arg  Asp  Pro  Arg  Leu  Pro  Ser  Ser  Ala  Ala  Ala  Ala  Ala  Ala
               675                      680                     685

Asp  Leu  Leu  Phe  Asp  Asn  Gln  Ser  Leu  Arg  Pro  Leu  Leu  Ala  Ala  Ala
          690                      695                     700

Ala  Ser  Ala  Pro  Asp  Ala  Ala  Asp  Ala  Leu  Ala  Ala  Ala  Ala  Ala  Ser
705                      710                     715                          720

Ala  Ala  Pro  Arg  Glu  Gly  Arg  Lys  Arg  Lys  Ser  Pro  Gly  Pro  Ala  Arg
                    725                     730                          735

Pro  Pro  Gly  Gly  Gly  Gly  Pro  Arg  Pro  Pro  Lys  Thr  Lys  Lys  Ser  Gly
                    740                     745                     750

Ala  Asp  Ala  Pro  Gly  Ser  Asp  Ala  Arg  Ala  Pro  Leu  Pro  Ala  Pro  Ala
               755                      760                     765

Pro  Pro  Ser  Thr  Pro  Pro  Gly  Pro  Glu  Pro  Ala  Pro  Ala  Gln  Pro  Ala
770                      775                     780

Ala  Pro  Arg  Ala  Ala  Ala  Ala  Gln  Ala  Arg  Pro  Arg  Pro  Val  Ala  Val
785                      790                     795                          800

Ser  Arg  Arg  Pro  Ala  Glu  Gly  Pro  Asp  Pro  Leu  Gly  Gly  Trp  Arg  Arg
               805                      810                     815

Gln  Pro  Pro  Gly  Pro  Ser  His  Thr  Ala  Pro  Ala  Ala  Ala  Ala  Ala  Leu
               820                      825                     830

Glu  Ala  Tyr  Cys  Ser  Pro  Arg  Ala  Val  Ala  Glu  Leu  Thr  Asp  His  Pro
               835                      840                     845

Leu  Phe  Pro  Val  Pro  Trp  Arg  Pro  Ala  Leu  Met  Phe  Asp  Pro  Arg  Ala
          850                      855                     860

Leu  Ala  Ser  Ile  Ala  Ala  Arg  Cys  Ala  Gly  Pro  Ala  Pro  Ala  Ala  Gln
865                      870                     875                          880

Ala  Ala  Cys  Gly  Gly  Gly  Asp  Asp  Asp  Asn  Pro  His  Pro  His  Gly
                    885                     890                     895

Ala  Ala  Gly  Gly  Arg  Leu  Phe  Gly  Pro  Leu  Arg  Ala  Ser  Gly  Pro  Leu
               900                      905                     910

Arg  Arg  Met  Ala  Ala  Trp  Met  Arg  Gln  Ile  Pro  Asp  Pro  Glu  Asp  Val
               915                      920                     925

Arg  Val  Val  Val  Leu  Tyr  Ser  Pro  Leu  Pro  Gly  Glu  Asp  Leu  Ala  Gly
     930                      935                     940

Gly  Gly  Ala  Ser  Gly  Gly  Pro  Pro  Glu  Trp  Ser  Ala  Glu  Arg  Gly  Gly
945                      950                     955                          960

Leu  Ser  Cys  Leu  Leu  Ala  Ala  Leu  Ala  Asn  Arg  Leu  Cys  Gly  Pro  Asp
               965                      970                     975

Thr  Ala  Ala  Trp  Ala  Gly  Asn  Trp  Thr  Gly  Ala  Pro  Asp  Val  Ser  Ala
               980                      985                     990

Leu  Gly  Ala  Gln  Gly  Val  Leu  Leu  Leu  Ser  Thr  Arg  Asp  Leu  Ala  Phe
          995                      1000                    1005

Ala  Gly  Ala  Val  Glu  Phe  Leu  Gly  Leu  Leu  Ala  Ser  Ala  Gly  Asp  Arg
     1010                     1015                    1020

Arg  Leu  Ile  Val  Val  Asn  Thr  Val  Arg  Ala  Cys  Asp  Trp  Pro  Ala  Asp
     1025                     1030                    1035                    1040

Gly  Pro  Ala  Val  Ser  Arg  Gln  His  Ala  Tyr  Leu  Ala  Cys  Glu  Leu  Leu
                    1045                    1050                    1055

Pro  Ala  Val  Gln  Cys  Ala  Val  Arg  Trp  Pro  Ala  Ala  Arg  Asp  Leu  Arg
               1060                     1065                    1070

Arg  Thr  Val  Leu  Ala  Ser  Gly  Arg  Val  Phe  Gly  Pro  Gly  Val  Phe  Ala
```

-continued

```
                                1075                            1080                                  1085
        Arg  Val  Glu  Ala  Ala  His  Ala  Arg  Leu  Tyr  Pro  Asp  Ala  Pro  Pro  Leu
             1090                1095                1100

Arg  Leu  Cys  Arg  Gly  Gly  Asn  Val  Arg  Tyr  Arg  Val  Arg  Thr  Arg  Phe
        1105                1110                     1115                          1120

Gly  Pro  Asp  Thr  Pro  Val  Pro  Met  Ser  Pro  Arg  Glu  Tyr  Arg  Arg  Ala
                            1125                     1130                     1135

Val  Leu  Pro  Ala  Leu  Asp  Gly  Arg  Ala  Ala  Ala  Ser  Gly  Thr  Thr  Asp
                       1140                     1145                     1150

Ala  Met  Ala  Pro  Gly  Ala  Pro  Asp  Phe  Cys  Glu  Glu  Glu  Ala  His  Ser
                  1155                     1160                1165

His  Ala  Ala  Cys  Ala  Arg  Trp  Gly  Leu  Gly  Ala  Pro  Leu  Arg  Pro  Val
             1170                     1175                     1180

Tyr  Val  Ala  Leu  Gly  Arg  Glu  Ala  Val  Arg  Ala  Gly  Pro  Ala  Arg  Trp
        1185                     1190                     1195                     1200

Arg  Gly  Pro  Arg  Arg  Asp  Phe  Cys  Ala  Arg  Ala  Leu  Leu  Glu  Pro  Asp
                            1205                     1210                     1215

Asp  Asp  Ala  Pro  Pro  Leu  Val  Leu  Arg  Gly  Asp  Asp  Gly  Pro  Gly
                       1220                     1225                     1230

Ala  Leu  Pro  Pro  Ala  Pro  Pro  Gly  Ile  Arg  Trp  Ala  Ser  Ala  Thr  Gly
                  1235                     1240                     1245

Arg  Ser  Gly  Thr  Val  Leu  Ala  Ala  Ala  Gly  Ala  Val  Glu  Val  Leu  Gly
             1250                     1255                     1260

Ala  Glu  Ala  Gly  Leu  Ala  Thr  Pro  Pro  Arg  Arg  Glu  Val  Val  Asp  Trp
        1265                     1270                     1275                     1280

Glu  Gly  Ala  Trp  Asp  Glu  Asp  Asp  Gly  Gly  Ala  Phe  Glu  Gly  Asp  Gly
                            1285                     1290                     1295

Val  Leu
```